US008138157B2

(12) United States Patent
Rubsamen

(10) Patent No.: US 8,138,157 B2
(45) Date of Patent: Mar. 20, 2012

(54) ANTIBIOTIC FORMULATION AND METHOD OF TREATMENT

(75) Inventor: Reid M. Rubsamen, Alamo, CA (US)

(73) Assignee: Flow Pharma, Inc., East Palo Alto, CA (US)

(*) Notice: Subject to any disclaimer, the term of this patent is extended or adjusted under 35 U.S.C. 154(b) by 213 days.

(21) Appl. No.: 12/758,602

(22) Filed: Apr. 12, 2010

(65) Prior Publication Data
US 2010/0291220 A1 Nov. 18, 2010

Related U.S. Application Data

(63) Continuation of application No. 11/749,369, filed on May 16, 2007, now abandoned, and a continuation-in-part of application No. 11/383,562, filed on May 16, 2006, now abandoned, which is a continuation-in-part of application No. 10/618,255, filed on Jul. 10, 2003, now abandoned, which is a continuation-in-part of application No. 10/195,046, filed on Jul. 12, 2002, now abandoned.

(60) Provisional application No. 60/821,668, filed on Aug. 7, 2006, provisional application No. 60/805,267, filed on Jun. 20, 2006, provisional application No. 60/326,675, filed on Oct. 2, 2001, provisional application No. 60/305,364, filed on Jul. 13, 2001.

(51) Int. Cl.
A61K 38/48 (2006.01)
A61K 31/70 (2006.01)
A61K 31/7036 (2006.01)

(52) U.S. Cl. .......... 514/23; 514/40; 424/489; 424/94.64

(58) Field of Classification Search .................... 514/23, 514/40; 424/489, 94.64
See application file for complete search history.

(56) References Cited

U.S. PATENT DOCUMENTS

| 2,804,424 | A | 8/1957 | Stirn et al. |
|---|---|---|---|
| 2,809,149 | A | 10/1957 | Cusumano |
| 3,933,832 | A | 1/1976 | Langbein et al. |
| 3,966,940 | A | 6/1976 | Pachter et al. |
| 3,987,797 | A | 10/1976 | Stephenson |
| 4,024,871 | A | 5/1977 | Stephenson |
| 4,191,743 | A | 3/1980 | Klemm et al. |
| 4,728,512 | A | 3/1988 | Mehta et al. |
| 5,124,155 | A | 6/1992 | Reich |
| 5,197,977 | A | 3/1993 | Hoffman, Jr. et al. |
| 5,366,756 | A | 11/1994 | Chesterfield et al. |
| 5,385,887 | A | 1/1995 | Yim et al. |
| 5,622,498 | A | 4/1997 | Brizzolara et al. |
| 5,633,014 | A | 5/1997 | Garza Flores et al. |
| 5,766,631 | A | 6/1998 | Arnold |
| 5,939,323 | A | 8/1999 | Valentini et al. |
| 5,972,366 | A | 10/1999 | Haynes et al. |
| 6,080,801 | A | 6/2000 | Draenert et al. |
| 6,090,996 | A | 7/2000 | Li |
| 6,143,037 | A | 11/2000 | Goldstein |
| 6,228,398 | B1 | 5/2001 | Devane et al. |
| 6,238,491 | B1 | 5/2001 | Davidson et al. |
| 6,309,669 | B1 | 10/2001 | Setterstrom et al. |
| 6,582,717 | B1 | 6/2003 | Shastri et al. |
| 6,743,446 | B2 | 6/2004 | Schwendeman et al. |
| 2002/0165608 | A1 | 11/2002 | Llanos et al. |
| 2004/0142043 | A1 | 7/2004 | Maeda et al. |

FOREIGN PATENT DOCUMENTS

WO WO0209669 2/2002

OTHER PUBLICATIONS

Hoen et al., "Osteomyelitis of the maxilla with associated vertical root fracture and *Pseudomonas* infection" Oral Surgery, Oral Medicine and Oral Pathology, 66(4):494-8 (1988).
Allen, Jr. et al., Ansel's Pharmaceutical Dosage Forms and Drug Delivery Systems, Eighth Edition, "Section III, Solid Dosage Forms and Solid Modified Release Drug Delivery Systems, Chapter 6, Powders and Granules" Lippincott Williams & Wilkins, pp. 186-203 (2003).
Bennett-Guerrero et al., "Gentamicin-Collagen Sponge for Infection Prophylaxis in Colorectal Surgery" The New England Journal of Medicine, (2010) 363:1038-49.
Boyes-Varley et al., Int. J. and Maxillafax. Surg., 17:138-141 (1988).
Choi et al., "Preparation and characterization of fentanyl-loaded PLGA microspheres: in vitro release profiles" International Journal of Pharmaceutics, 234:195-203 (2002).
Faisant et al., "PLGA-based microparticles: elucidation of mechanism and a new, simple mathematical model quantifying drug release" European Journal of Pharmaceutical Sciences, 15:355-366 (2002).
Lobato et al., "Assessment of Bonelike graft with a resorbable matrix using an animal model" Thin Solid Films, 515:362-367 (2006).
Sendil et al., "Assessment of biodegradable controlled release rod systems for pain relief applications" J. Biomater. Sci. Polymer Edn., 13(1):1-15 (2002).
Siepmann et al., "Mathematical modeling of bioerodible, polymeric drug delivery systems" Advanced Drug Delivery Reviews, 48:229-247 (2001). Wagenaar et al., "Piroicam release from spray-dried biodegradable microspheres" Biomaterials, 15(1):49-54 (1994).

(Continued)

Primary Examiner — Raymond Henley, III
(74) Attorney, Agent, or Firm — Karl Bozicevic; Bozicevic, Field & Francis LLP

(57) ABSTRACT

A formulation comprised of particles which may be in groups and are comprised of a biocompatible polymer and an antimicrobial drug for controlled release of the drug is disclosed. The particles may be in an aqueous solution comprising thrombin and be dispersed in a gel. The formulation is administered to an area such as an open wound having an orthopedic implant therein and provides a therapeutically effective level of drug to the patient over therapeutically effective period of time.

16 Claims, 8 Drawing Sheets

ANTIBIOTIC FORMULATION AND METHOD OF TREATMENT

CROSS-REFERENCES

This application claims the benefit of priority of earlier filed U.S. Provisional Patent Application Ser. No. 60/821,668 filed Aug. 7, 2006 and of earlier filed U.S. Provisional Patent Application Ser. No. 60/805,267 filed Jun. 20, 2006 and is a continuation-in-part of U.S. application Ser. No. 11/383,562 filed May 16, 2006 which is a continuation-in-part of earlier filed U.S. application Ser. No. 10/618,255 filed Jul. 10, 2003 (now abandoned) which is a continuation-in-part of earlier filed U.S. application Ser. No. 10/195,046 filed Jul. 12, 2002 (now abandoned) which claims priority to provisional Application Ser. No. 60/326,675 filed Oct. 2, 2001 and provisional Application Ser. No. 60/305,364 filed Jul. 13, 2001 all of which applications are incorporated herein by reference and to which application priority is claimed.

FIELD OF THE INVENTION

The invention relates to a formulation of controlled release particles which may be dispersed in a gel and/or a therapeutic solution to provide an antimicrobial effect to the surrounding area.

BACKGROUND OF THE INVENTION

In order to improve the effectiveness and functionality of wound dressings and surgical implants, various attempts have been made to incorporate them with a variety of medicaments such as antibiotics, analgesics, and the like—see U.S. Pat. No. 5,972,366.

Examples of antibacterial wound dressings are disclosed in U.S. Pat. No. 4,191,743 to Klemm et al., U.S. Pat. No. 2,804,424 to Stirn et al., and U.S. Pat. No. 2,809,149 to Cusumano. Similarly, U.S. Pat. No. 3,987,797 to Stephenson discloses a suture rendered antimicrobial.

Dressings which attempt to promote wound healing are disclosed in U.S. Pat. No. 5,124,155 to Reich. Many prior art surgical bandages and dressings which incorporate medications are made by soaking the material in an aqueous solution of the medicine. This can render the carrier brittle and inflexible upon drying. Moreover, it is difficult to control the rate of release of the medicament, or its effect on peripheral tissues, when it is applied to the carrier dissolved in a liquid state. Also, many important medicines are water insoluble and cannot be applied by this technique. Alternatively, the medicament is applied to the dressing or implant as a powder or dust which is quickly released and possesses a danger that large drug particles may irritate tissue or enter the circulatory system where they can block capillaries.

In addition to externally applied dressings, it is also known to impregnate an implantable surgical material with a medicament. For example, U.S. Pat. No. 5,197,977 to Hoffman Jr. et al. disclose a synthetic vascular graft that is impregnated with collagen and a medicament.

Additionally, Boyes-Varley et al. in Int. J. and Maxillafac. Surg. 1988; 17:138-141, describe the use in an animal study of a the Gelfoam® brand sponge with a saline solution of medicaments. However, the Physicians' Desk Reference, (Medical Economics, Co., Oradell, N.J.) 1992 edition warns that "it is not recommended that Gelfoam® be saturated with an antibiotic solution or dusted with antibiotic powder." A similar warning is provided with the entry of another popular surgical implant—the Surgicel® brand absorbable hemostat—which states that "the Surgicel® hemostat should not be impregnated with anti-infective agents."

One well known method of suppressing infection is to provide relatively high levels of an antibiotic systemically. For example, high levels of gentamicin are systemically administered to patients in order to prevent infection in high risk situations, such as patients subjected to severe trauma whose wounds may well have been compromised with infectious bacteria. High systemic levels can have adverse effects including loss of hearing. Another method employed is to dissolve an antibiotic such as gentamicin in a solution such as water and spray the wound thoroughly with the solution. In some situations the solution is so dilute as to be ineffective in preventing infection. Accordingly, another alternate method which is employed is to simply put high concentrations of gentamicin powder into the wound. High concentrations applied locally are known to hinder bone healing. Further, although high concentrations can be applied the powder may not last sufficiently long in order to prevent infections after a considerable amount of time has passed. Accordingly, there remains a need for a formulation which can avoid the problem of high level systemic administration and provide for local administration at sufficient levels over a sufficiently long period of time so as to suppress infection.

In view of such the present invention is proposed.

SUMMARY OF THE INVENTION

Formulations are disclosed which are comprised of antimicrobial particles, a thrombin solution, and a biocompatible gel having the particles dispersed therein. The antimicrobial particles may be provided in a plurality of groups (2, 3 or more) of different size spheres. The spheres may be comprised of one or more antimicrobial agents and a controlled release polymer such as poly lactic glycolic acid (PLGA) or other suitable, biocompatible material.

The formulation may be comprised of the groups of different sizes particles by themselves, in an aqueous solution which may include thrombin or dispersed in a gel which may include thrombin. Each group of spherical particles may consist of multiple particles which are all substantially the same size which together with other groups are designed to provide a combination of different drug release rates when the formulation is deployed or implanted and provide a relatively constant level of drug to the surrounding area. The formulation provides a concentration of about 30 micrograms/ml±25 micrograms per ml over a period of time of about 1 to 7 days, or 2 to 5 days or about 72 hours±12 hours. The different groups of particles are formulated together and may be dispersed in a gel such as Floseal™ or other biocompatible gel material to obtain a desired drug release profile.

In one embodiment the groups of particles of the antimicrobial are put into an aqueous solution of thrombin (e.g. 5 cc providing 20,000 units thrombin/cc±20%) and this aqueous solution is then combined with a biocompatible gel such as Floseal™. As the release rate of one group of particles is decreasing (or the drug released from the group is being metabolized out of the system) the release rate of another group of particles is increasing (or drug from one group is being added to the system) so that the combined groups of particles making up the formulation provide a substantially constant level of drug (30 mcg/ml±25 mcg/ml) over a therapeutically effective period of time (1-7 days). The concentrations of antimicrobial drug and BMP obtained at a wound and the release rate of these drugs may be varied with different antimicrobial drugs and patient conditions to obtain a desired end result.

Formulations of particles may be divided into separate disposable packets which may be a single use syringe wherein each syringe of formulation includes a plurality of groups of spheres wherein the spheres of each group of spheres are all of substantially the same size. Thus, the packet may include 2, 3, 4 or more groups of spheres with a typical formulation being comprised of three groups of spheres in a small, medium, and large size. The packet of formulations is specifically designed so as to obtain a desired therapeutic effect. The desired therapeutic effect of the antimicrobial particles is to provide a therapeutic level of antibiotic such as gentamicin in a wound site over a period of time which is therapeutically effective in preventing infection. If the level of the antimicrobial drug drops too low then the antimicrobial effect is lost. However, if the level is raised too high the drug becomes toxic to surrounding tissue such as hindering bone growth. Still further, if the therapeutic level of the drug is not maintained for a sufficiently long period of time infection can occur. If the therapeutic level of the antimicrobial level is maintained for too long of a period of time there may also be undesirable results such as the development of microbes which are resistant to the drug being used. Thus, it is important to adjust the formulation so that the concentration of the drug delivered to the target area is not too low or too high and so that the drug is delivered for a sufficiently long period of time but not a period which is too long.

In one embodiment of the invention the formulation comprised of antimicrobial spheres is first added to an aqueous solution which may be a saline solution comprising thrombin. The spheres are mixed in the aqueous solution and then combined with an aqueous biocompatible gel such as Floseal™. The combination may be made within a syringe where the gel and solution can be intermixed in a manner so as to allow the particles to be dispersed throughout the combination of the aqueous solution and gel. In this form the formulation is injected into the wound site.

The antimicrobial drug or drugs will have therapeutic levels locally but substantially undetectable levels systemically. The amount of the antibiotic only a few centimeters from the site where the gel is present (e.g. 5 cm or more) is substantially undetectable. In the target area the level is 30 mcg/ml±25 mcg/ml. Although the formulation is administered and provides a therapeutic level within the target area the controlled release formulation of the particles is designed such that the level does not reach a toxic level or provide excess which would be wasted. Thus, although antimicrobial drug could be administered with some drug not being present within controlled release spheres to obtain immediate release the amount of antibiotic for immediate release is therapeutic and not toxic with respect to substantially inhibiting bone growth. A powdered form of the antibiotic may be mixed with the aqueous solution which is further comprised of thrombin. The aqueous solution comprising the antibiotic and thrombin can then be mixed with the gel and injected into a wound site in manner such that the formulation has the particles distributed throughout the formulation injected into the wound site.

The formulation is also designed such that antibiotics are administered over a therapeutically effective period but the antibiotic is not released continually over many weeks (or much beyond 7 days) in order to avoid building up antibiotic resistance. Thus, the controlled release formulation of the invention is different from quick release formulation which provides toxic levels initially but substantially no levels after a short period of time and also different from formulations where an antibiotic is embedded within a bone cement and seeps out over a very long period of time allowing for the development of antibiotic resistance. Thus, the antibiotic level produced with a formulation of the invention is within a therapeutic range sufficient to inhibit infection (above 5 mcg/ml) but insufficiently high to be toxic to the bone (below 55 mcg/ml) and provides that level for a duration long enough (1-7 days) to prevent infection based on bacteria which may have entered the wound initially but does not maintain the level over a sufficiently long period of time so as to result in the development of antibiotic resistance.

Although the formulation can be produced using a wide range of different antibiotic antiviral and antimicrobial compounds it can be readily prepared using very inexpensive widely known FDA approved antibiotics such as gentamicin. Although the spheres within the formulation can be produced using a wide range of different polymers the formulation is typically produced using a biocompatible widely used and accepted polymer such a polylacticglycolic acid (PLGA).

The methodology described here substantially reduces the trial and error of producing a controlled release formulation. This is done by using particles of a known size (volume and surface areas±10%) shape (spherical) and dissolution rate within an environment to which the particles are delivered. Because all the particles of any given group have substantially the same surface area from one particle to another the dissolution rate of a given particle and the group of particles can be calculated mathematically based on a known dissolution rate of a particle of known surface area. Particles in the formulation preferably have a spherical shape and a diameter in a range of from about 2 microns to about 40 microns about 10 microns±1 micron. The particle types may include particles comprised of drug alone, drug and polymer mixed and/or drug coated with polymer.

A typical formulation can be comprised of two groups of particles wherein the first group is comprised of particles having a diameter of about 6 microns and the second group comprised of particles having a diameter of about 20 microns. These particles have spherical conformations and each particle within each group has approximately the same size and shape with a differential ±10%. Although the particles may be configured in different ways such as having antibiotic drug on the inside and coated polymer on the outside, a typical formulation also includes spheres where the drug and polymer are intermixed. Such spheres are easily produced by mixing the antibiotic in the polymer and thereafter forming the spheres. Spheres can be produced using a technology such as that described within U.S. Pat. No. 6,241,159 issued Jun. 5, 2005 and U.S. Pat. No. 6,174,469 issued Jan. 16, 2001 as well as related issued U.S. and non-U.S. patents to Alfonso Ganan-Calvo all of which are incorporated herein by reference in their entirety to disclose and describe methods of making uniform sized small particles.

An aspect of this invention is to show that in addition to relying on the chemical properties of injected microparticles for their controlled release characteristics, the physical size of these particles can be used to provide another layer of control over the release profile because that the physical size of particles in different groups of particles can be controlled precisely as can the total surface area of all the particles in the group combined. When the particles are very small in size (e.g. 1-40 micrometers) the surface area differential from one group to the next can be made quite large by small changes in diameter.

Poly (lactide-co-glycolide) polymers (PLGA) can be used as an excipient in the creation of precisely sized microparticles for attachment to a device such as a surgical screw to produce a sustained release profile by using short chain PLGA polymer allowing the PLGA to be manipulated during the formulation process without the use of organic solvents.

Other polymer excipients can be used if they are pharmaceutically acceptable and biocompatible with the surrounding tissue e.g. bone. Another useful polymer is PDLLA which is poly-dl-lactic acid which has a higher glass transition point (about 45°-55° C.) than PLGA having a glass transition point of about 30°-40° C.

Unlike an approach which might rely solely on the chemical composition of microparticles as a means for creating controlled release formulations, the present invention relies additionally on precise sizing of the microparticles and the use of at least two different sizes of microparticles in the formulation. By exploiting the precise differences in surface area to volume ratio in the different populations of microparticles in the formulation, there is intrinsically less reliance on the chemistry of the particles to produce a sustained levels of the drug in the surrounding area. By relaxing the requirement that the chemistry will have the predominant effect on the controlled release behavior a simpler chemistry can be employed which is easier and less costly to manufacture, and which avoids the use of organic solvents during its production period. For example, short chain PLGA polymer can be employed which can be processed without the use of organic solvents.

Poly (lactide-co-glycolides) (PLGA) compositions are commercially available from Boehringer Ingelheim (Germany) under the Resomer mark e.g. PLGA 50:50 (Resomer RG-502), PLGA 75:25 (Resomer RG-752) and d, l-PLA (Resomer RG-206) and from Birmingham Polymers (Birmingham, Ala.). These copolymers are available in a wide range of molecular weights and ratios of lactic acid to glycolic acid.

An aspect of the invention is a biocompatible gel incorporating spherical particles which provide a desired drug release profile by combining a plurality of different groups of particles wherein each group consists of particles all of which have a known size, number and shape so that the combined groups provide a rate of dissolution in a known environment where the gel is implanted.

Another aspect of the invention is that it be comprised of a plurality (2 or more) of different groups of particles wherein the particles within each group are substantially the same in size and shape (±10%) and are different from one group to another group as regards the drug release profile of the particles in a particular group. The particles preferably have a size in a range of from about 1 to about 100 micrometers in diameter and more preferably about 2 to 70 or 2 to 40 or 4 to 30 micrometers in diameter.

In additional to producing formulations comprised of different groups of particles the formulation of particles is being sealed in sterile disposable containers with or without gel and/or thrombin both of which are generally added at the point of administration. The formulation of particles may be themselves considered devices because they are comprised of polymer and drug or they may be coated onto or administered along with devices. This includes coating the formulations onto orthopedic surgical devices including screws (solid and cannulated), wires, plates, artificial joint components and other hardware for fixing fractures and stabilizing otherwise weakened parts of the skeletal systems all anchor into bone. Bone is a living tissue which is susceptible to infection. The incidence of bone infection (osteomyelitis) following orthopedic surgery and hardware placement can be as high as 2%-16% in the context of trauma where broken bones are reduced through open incisions and subsequently internally fixated with metal hardware. The invention aids in reducing nephrotoxicity and ototoxicity which are caused by aminoglycosides.

In order to reduce the likelihood of infection, surgeons generally administer systemic antibiotics (typically given intravenously prior to surgery) and antibiotic-containing irrigation solutions used to clean the wound. These approaches have the common disadvantage that the antibiotic concentration is not being maximized where it is most needed i.e. at the interface between the hardware and the bone. This location is important because the presence of a foreign body increases the likely hood of local infection because bacteria can become trapped between the hardware device and the bone itself.

A process useful in producing small encapsulated particles of uniform size and shape can be used to encapsulate commonly used antimicrobials including antibiotics such as those from the amino glycoside group (e.g. kanamycin, gentamycin, tobramycin, vancomycin) those from the cephalosporin group (e.g. ancef, cefotitan) those from other groups and/or comprised of combinations of drugs (e.g. Unasyn) with a biodegradable polymer such as poly lactic glycolic acid (PLGA). These precisely sized antibiotic-containing spheres can be produced in specific, different sizes so as to (a) produce a time-release profile of antibiotic into bone adjacent to hardware over a period of hours, days, weeks or months and/or (b) to specifically target naturally occurring or fabricated imperfections in the coated hardware to ensure that the antibiotic-containing spheres are deposited in these crevices in a manner causing them to remain in place after the coating process and during and after implantation of the hardware into a patient.

An aspect of the invention is a packet of formulation comprised of a first group and a second group of particles. The particles are preferably spherical and are comprised of a biocompatible polymer and a pharmaceutically active drug which may be an antimicrobial such as an antibiotic. The particles are generally present in an amount of about 100 or more particles wherein all of the particles within the group have substantially the same size with a margin of error ±10%. There may be a plurality of groups of particles wherein the particles within the one group are the same with respect to each other but are different with respect to particles within another group. Further, the particle within one group have a rate of dissolution which is different from the particles within other groups thereby making it possible to provide a controlled release of the drug into the surrounding environment.

Another aspect of the invention is a formulation comprised of a plurality of antimicrobial particles which particles are comprised of an antimicrobial drug and a biocompatible polymer. The particles are dispersed in a pharmaceutically acceptable carrier which may be a biocompatible gel or absorbable collagen sponge. The particles may have uniform size and shape or may be designed so as to have irregular sizes and shapes. The formulation is designed such that when it is placed in the wound the formulation provides a therapeutically effective dose of the antimicrobial drug over a period of time of greater than 1 day and less than 7 days. The dose is above 5 micrograms per milliliter and below 100 micrograms per milliliter and is preferably 35 micrograms per milliliter±25 micrograms per milliliter. Further, the dose is local and extends outward from the target site of implantation to a distance of not more than 5 cm. The antimicrobial drug is substantially undetectable systemically.

Yet another aspect of the invention is a wound having a formulation as described above inserted therein. The wound is provided with a therapeutically effective dose of the antimicrobial drug over a therapeutically effective period of time. The wound may be any type of wound including a wound caused by trauma, a surgical wound site, or a combination of the two which may have an orthopedic device inserted therein.

Still another aspect of the invention is a method of treatment whereby a surgical wound is created either from an initial point of entry or in combination with a trauma wound. Surgical procedures are performed for the implantation of an orthopedic device. The wound is washed with solution in an attempt to clean the wound. The solution used for washing may include saline solution and the saline solution may be comprised of an antimicrobial compound. Prior to closing the wound a formulation of the invention as described above is administered.

Another aspect of the invention is a formulation comprised of a biocompatible polymer and a plurality of groups of particles. The particles are comprised of a biocompatible polymer and a drug such as an antibiotic e.g. an aminoglycoside.

Another aspect of the invention is the formulation comprised of the groups of particles present in an aqueous solution which may be an aqueous sealing solution which solution may be further comprised of thrombin.

In another aspect of the invention is the aqueous solution as described above with the particles therein combined and mixed thoroughly with a biocompatible gel.

Still yet another aspect of the invention is groups of particles of biocompatible polymer within antibiotic therein dispersed in a biocompatible gel such as Floseal™ which gel may be further comprised of thrombin.

In another aspect of the invention is a method comprising including groups of spherical particles comprised of biocompatible polymer and antibiotic into an aqueous solution having antibiotic in the solution and injecting the solution into a wound site.

Another aspect of the invention is a method comprising providing particles which may be in first and second groups of particles as defined here into an aqueous solution having therein antibiotic and thrombin and mixing this solution with biocompatible gel such as Floseal™ and injecting the mixture into a wound site.

Another aspect of an embodiment of this invention is to provide an orthopedic implant hardware coated with microencapsulated antimicrobial for infection-prevention.

Another aspect of an embodiment of this invention is to provide a plurality of polymer-coated particle sizes in order to (a) maximize the adherence of these particles to surface indentions created in the hardware and (b) to produce a desired time-release profile of into bone.

Another aspect of an embodiment of this invention is to provide orthopedic hardware with antimicrobial maximized for its delivery of the antibiotic to the clinically relevant zone without exposing the patient to chronic, systemic doses of antimicrobial.

Another aspect of an embodiment of this invention is to provide orthopedic implant components coated in this fashion individually packaged with an appropriate secondary over-wrap (e.g. a hard plastic cylinder with a twist-off top) in order to preserve the encapsulated antimicrobial shelf-life.

Another aspect of an embodiment of this invention is to provide coated orthopedic implant components packaged with temperature QC tags to ensure that the suggested ambient temperature is not violated.

These and other aspects of various embodiments of the invention will become apparent to those persons skilled in the art upon reading the details of the devices and methods as more fully described below.

BRIEF DESCRIPTION OF THE DRAWINGS

The invention is best understood from the following detailed description when read in conjunction with the accompanying drawings. It is emphasized that, according to common practice, the various features are schematic and of the drawings are not to-scale. On the contrary, the dimensions of the various features are schematic and arbitrarily expanded or reduced for clarity. Included in the drawings are the following figures.

DETAILED DESCRIPTION OF THE INVENTION

Figure 1:
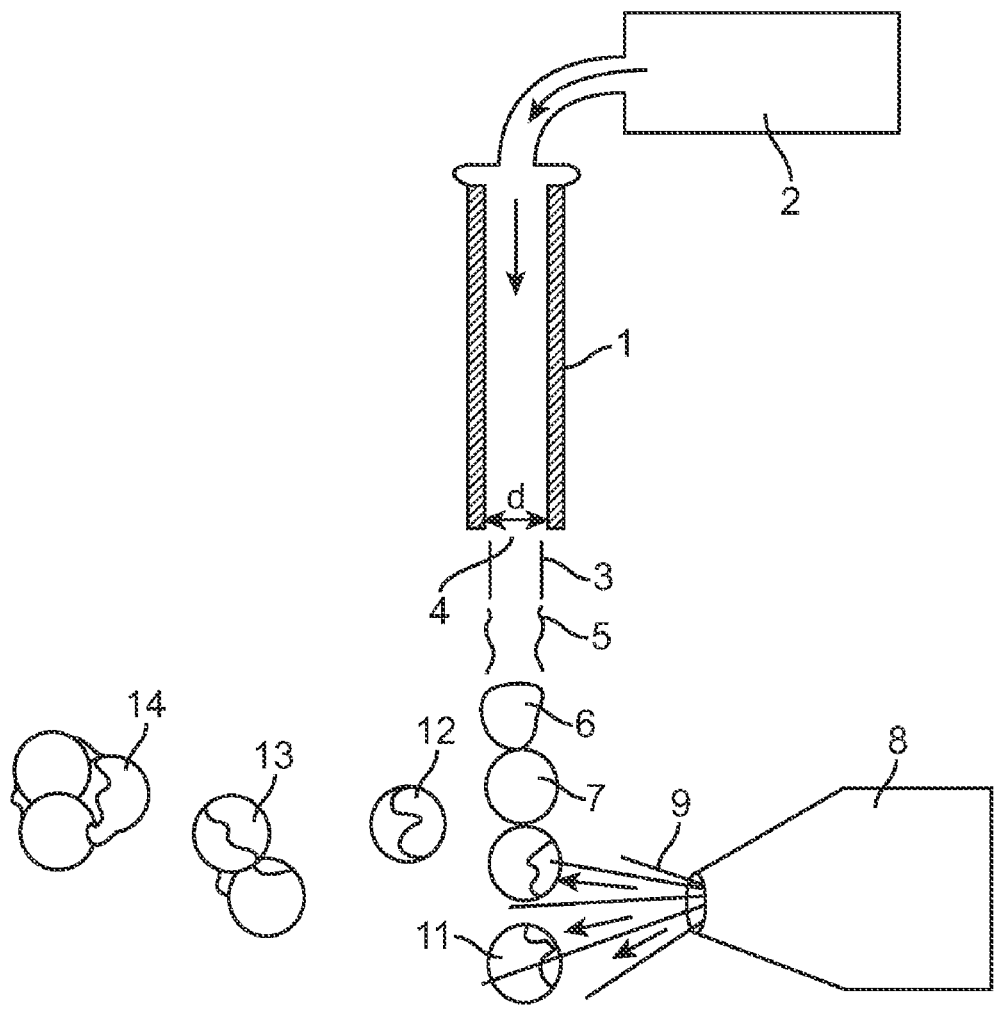
FIG. 1 is a schematic view of a spray drying device which produces particles of random sizes and shapes.

Before the present formulations, devices and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a controlled release sphere" includes a plurality of such spheres and reference to "the screw" includes reference to one or more screws and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

"Osteomyelitis" is an inflammation or an infection in the bone marrow and/or surrounding bone. The disease may be classified as either acute or chronic, depending on the length of time the infection or symptoms persist. Symptoms may include pain, warmth and/or swelling in the bone. Chronic osteomyelitis may last for years, with slow death of bone tissue from a reduced blood supply. Signs and symptoms may be absent, however, causing difficulty in diagnosing the chronic infection. The invention includes treating osteomyelitis in connection with surgical implants and in particular surgical screws.

Pathogens infect bone in posttraumatic osteomyelitis after a recent fracture. Bacteria, fungus and other microorganisms are typically the causative agents. The more susceptible a bone is to fracturing, the greater the chances of becoming infected and developing disease. Trauma from recent injuries and diabetes are major risk factors for osteomyelitis. The bone can be directly infected from the wound or indirectly via the blood from another site of infection, called hematogenous osteomyelitis. The vertebrae and pelvis are often affected in adults in this blood-borne variety, while children are usually affected in long bones.

The incidence of osteomyelitis after open fractures is reported to be 2% to 16%, depending significantly on the grade of trauma and the type of treatment administered. Prompt and thorough treatment help reduce the risk of infection, decreasing the probability of developing osteomyelitis. This is particularly important for patients with the following risk factors: diabetes, altered immune states and recent trauma. The tibia is the most frequent site of posttraumatic osteomyelitis, since it is the most vulnerable bone with the least vigorous blood supply in the body.

The classification of osteomyelitis can be broken down into the following categories: exogenous osteomyelitis (47%), secondary to vascular insufficiency (34%) and hematogenous osteomyelitis (19%). The implantation of an orthopedic device (pins, plate, screws, artificial joint) can also seed infection as a nidus for pathogens, and therefore create post-operative osteomyelitis.

Risk factors include the growing skeleton. Any bone can be affected but it is usually the weight-bearing bones before the physis has closed. At the physis on the metaphyseal side, end arteries form a capillar loop which may rupture following minor trauma. This region of blood stasis may attract circulating bacteria everybody has bacteria circulating, periodically. Once brought to the area through the vascular system, bacteria can set up shop in surrounding tissues.

The presence of bacteria alone in an open fracture is not sufficient to cause osteomyelitis. In many cases, the body's immune system is capable of preventing the colonization of pathogens. The micro-environment determines whether infection occurs. The timing and extent of treatment are critical in determining whether infection develops. The likelihood of developing osteomyelitis increases with impaired immune function, extensive tissue damage, or reduced blood supply to the affected area. Patients with diabetes, poor circulation or low white blood cell count are at greater risk.

Bacterial or fungal infection cause most osteomyelitis. Infection induces a large polymorphonuclear response from bone marrow, particularly *staphylococcus aureus, streptococcus* and *haemophilus influenza. Staphylococcus* infection predominates today and before the era of antibiotics.

The diagnosis of osteomyelitis may be made from clinical, laboratory and imaging studies. When the skeletal system is involved, pain, fever and leukocytosis (an increase in white blood cell count due to infection or inflammation) occur. The affected area is painful. Initial x-rays are typically normal. As early as 4 days, an area of lucency may be seen on x-ray.

Usually, the changes are not recognized until 10 days or two weeks have passed. Subperiosteal new bone formation in the affected area is present, representing periosteal elevation from encroaching pus. If not successfully treated, pus enlarges the bone appearing as increased lucency, which surrounds sclerotic, dead bone. This inner dead bone is called the sequestrum (sequestered from blood supply), and the outer periosteal reaction laminates to form the involucrum.

Draining sinuses develop when the pressure of pus exceeds the containment of the soft tissue. This further deprives the bone of its blood supply. This in turn harbors more bacteria, and the process cannot be reversed until extensive debridement of the area occurs-until the environment changes to one that promotes healing.

Osteomyelitis is an infection involving the bone. It often afflicts the growing individual. The bones usually affected are the weight-bearing bones before the physis has closed. Exogenous osteomyelitis occurs from trauma, sometimes as trivial as falling on a stick. Hematogenous osteomyelitis occurs from bacteria circulating in the bloodstream. Acute and chronic subtypes are classified according to the timing and duration of the infection.

Publications providing further details regarding osteomyelitis include the following:

Dirschl D R, Almekinders L C. Osteomyelitis. Drugs. 1993; 45: 29-43.
Ehara S. Complications of skeletal trauma. Radiol Clin North Am. 1997; 35: 767-781.
Sammak B, Abd El Bagi M, Al Shahed M, et al. Osteomyelitis: a review of currently used imaging techniques. Eur Radiol. 1999; 9: 894-900.
Waldvogel F, Medoff G, Swartz M. Osteomyelitis: a review of clinical features, therapeutic considerations and unusual aspects (I). N Engl J. Med. 1970; 282: 198-206.
Widmer A F. New developments in diagnosis and treatment of infection in orthopedic implants. Clin Infect Dis. 2001; 33: S94-S106.

The terms "treatment", "treating" and the like are used herein to generally mean obtaining a desired pharmacological or physiological effect. The effect may be prophylactic in terms of completely or partially preventing a disease such as an infection or symptom thereof and may be therapeutic in terms of partially or completely curing a disease and/or adverse effect attributed to the disease or infection. "Treatment" as used herein covers any treatment of any disease and specifically preventing growth of harmful infectious bacterial, fungal, parasitic, and viral infections, in a mammal, particularly a human, and includes:

(a) preventing the infection from occurring or developing in the subject which may be predisposed to the infection but has not yet been diagnosed as having it;

(b) inhibiting the infection, i.e. arresting its development; or (c) relieving the infection, i.e. causing regression of the infection. Treatment may be specifically directed towards treating patients with wounds caused by trauma and/or surgery and in particular bone damage and includes treatment that involves the use of surgical gels, glues and implants in order to prevent infection or more particularly preventing osteomyelitis. In connection with the invention treating can comprise using formulations of the invention during surgical procedures such as the injection and use of surgical gels (e.g. Florseal™) and the implantation of orthopedic components with antimicrobial controlled release compositions bound to the surface of the implant so as to treat (prevent) osteomyelitis.

Formulations

Figure 7:
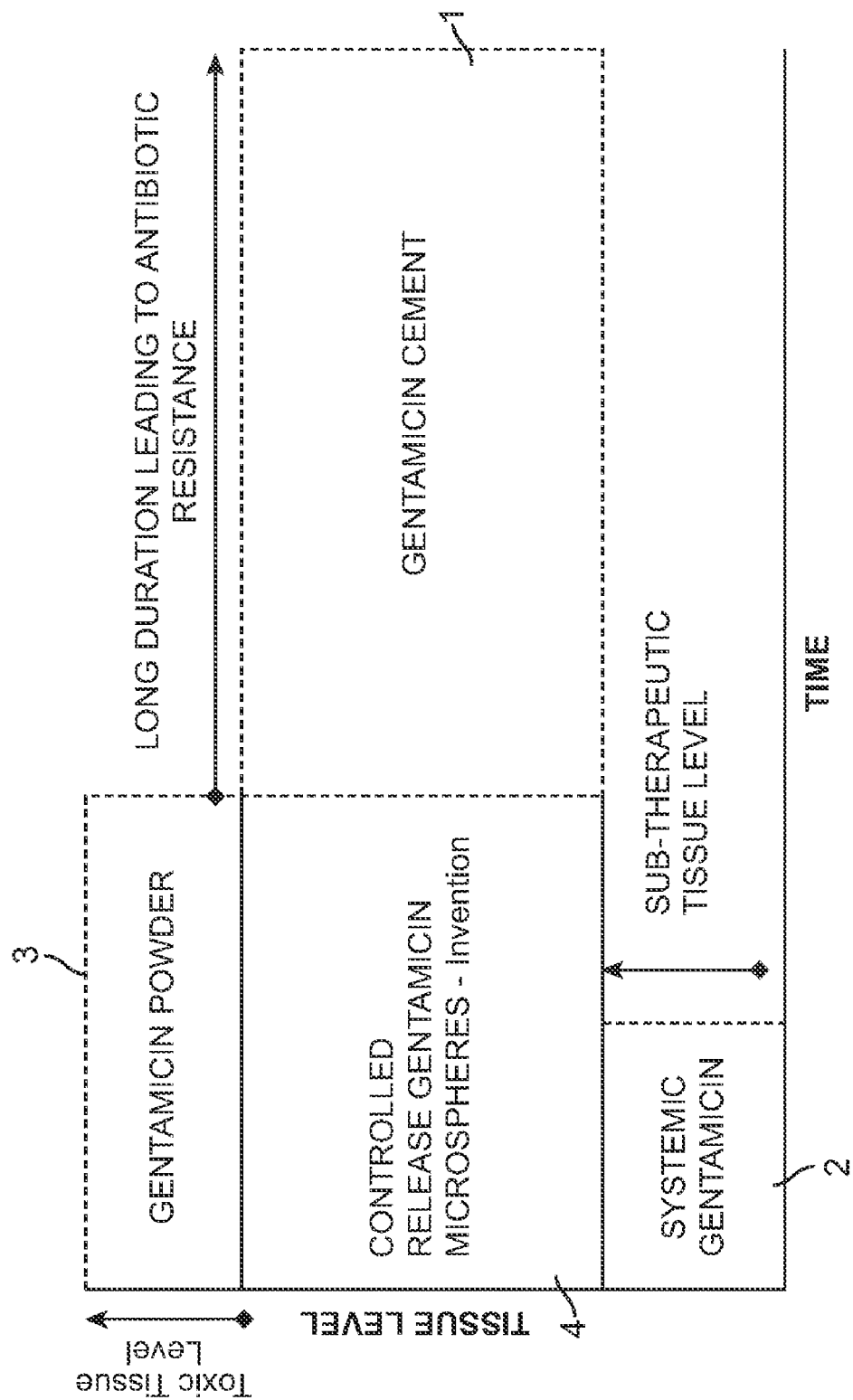
FIG. 7 is a schematic diagram showing areas where a given concentration of antibiotic might be obtained over time with different delivery mechanisms including formulations of the invention.

In one form a formulation of the invention might be comprised of two groups of particles. The particles within each group may have the same size and shape e.g. spherical and vary in size ±10%. However, the particles in the first group will be different from the particles in the second group in a manner which results in the first group dissolving at a rate which is faster than the particles in the second group. The particles are comprised of a biocompatible polymer and a drug which drug may be an antimicrobial such as an antibiotic which may be gentamicin. Other groups of particles and particles of different sizes may be added to such a formulation in order to provide variations on the release profile in order to get a release rate similar to that shown in FIG. 8. The object is to obtain release at a low level (25 mcg/ml±25 mcg/ml) at the target area over a sufficiently long period of time (1-7 days) so as to prevent infection and to avoid reaching toxic levels shown in FIG. 8. Another aspect of the invention is to maintain the control of the release rate in a manner such as shown in FIG. 7 so that the release does not continue over a very long period of time (less than about 7 days and generally around 72 hours±12 hours) so as to result in the development of antibiotic resistance.

In addition to the basic formulation may include any mixtures of particles in a solution, in a biocompatible gel or combination of the solution and gel with thrombin therein. More specifically, the formulation may be comprised of the particles included within a separate sealed packet. That packet may be opened just prior to use and added to an aqueous solution. That aqueous solution may be a saline solution and may be further comprised of a therapeutically effective amount of thrombin. The particles in the solution which may contain thrombin may be administered directly to a patient. In another formulation of the invention particles or the groups of particles contained within the sealed packet are opened just prior to administration and added to a biocompatible gel which may have thrombin therein. The particle formulations are mixed into the gel so that the particles are evenly distributed throughout the gel. Thereafter, the formulation comprised of the gel having particles dispersed therein is administered to a patient such as by injecting the formulation from a syringe.

In yet another embodiment the particles or groups of particles contained within the packet or packets are removed from the packet just prior to use and added to the aqueous solution as described above. Further, just prior to administration that aqueous solution is intermixed with a biocompatible gel such as Floseal™. The particles, solution (which may contain thrombin) is thoroughly mixed with a compatible gel such as Floseal™. A combination of particles, thrombin solution and Floseal™ may be thoroughly mixed within a syringe or other appropriate container. After dispersing the solution and particles throughout the gel the formulation is administered to a patient such as by injection into a wound site.

Figure 8:
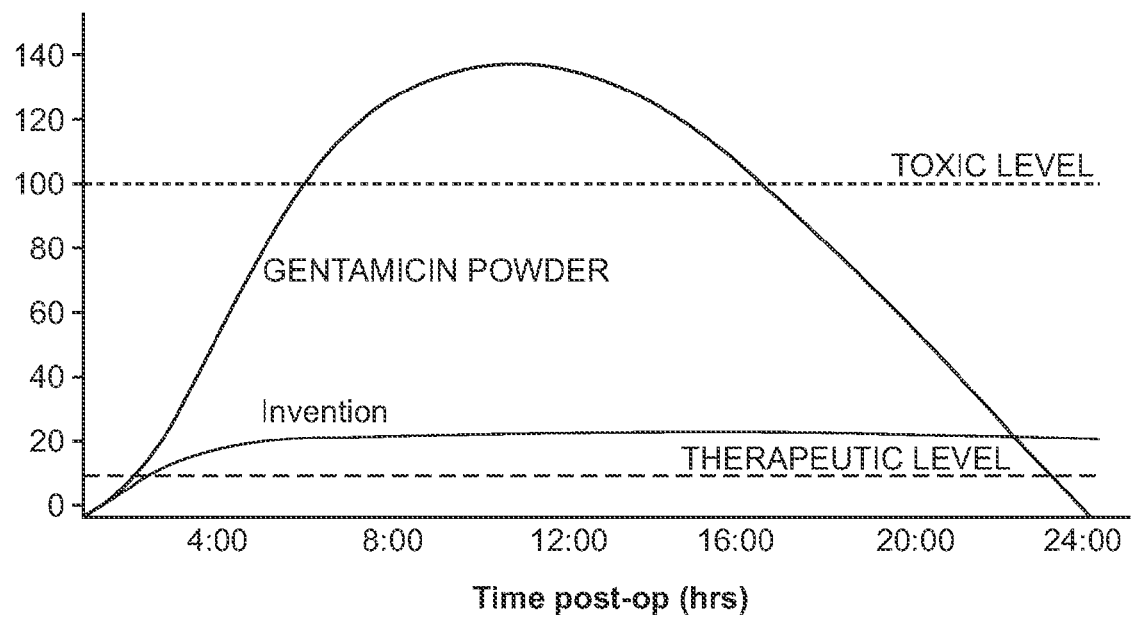
FIG. 8 is a schematic diagram showing a proposed drug release rate of the invention as compared with immediate release gentamicin powder.

Those skilled in the art will understand that the drug release profile can be affected by the size and number of the particles as described below and further affected by the amount of solution and gel. Those skilled in the art having this disclosure before them will understand that it is preferable to create formulations which have desired drug release profiles shown within FIGS. 7 and 8 and provide an efficacious but non-toxic dose over a sufficiently long period to prevent infection and avoid creating antibiotic resistant bacteria. More specifically, the drug which may be an antibiotic such as gentamicin is preferably not administered systemically but rather locally. Further, it is administered in an amount so as to obtain a therapeutic level but not a toxic level 30 mcg/ml±25 mcg/ml. Still further, the therapeutic level is preferably maintained over a sufficiently long period of time so as to prevent infection (over 24 hours) but not long enough so as to develop antibiotic resistance (less than 7 days). Still further, low levels of drug release over long periods of time as shown in FIG. 8 are preferred.

Those skilled in the art will understand that any of the embodiments of the invention described above can be further supplemented by adding some quick release drug which may be a powdered form of a drug such as a powdered form of an antibiotic such as gentamicin. Thus, the powdered drug can be combined with the particles or groups of particles in the thrombin containing solution, or combined with the particles, thrombin solution and gel. Those skilled in the art will understand that the various components of the formulation can be intermixed in a manner so as to evenly disperse the components throughout the formulation or the different components can be added separately to a wound site. With there various formulations in mind those skilled in the art should consider the mathematics of the controlled release particles as described further below.

Mathematics of Controlled Release Particles

The formulation packets are comprised of particles or groups of particles based on mathematics. For any given particle having a given amount of surface area the rate of dissolution will decrease as the particle dissolves and the total available surface area decreases. Thus, a spherical particle with two square units of available surface area which dissolves at a rate of X per unit of time will be dissolving at a rate of X/2 per unit of time once the particle has dissolved so that it has one square unit of available surface area. This assumes a constant environment unaffected by the dissolution.

By combining two different particles each comprised of the same material but of a different size the combined rate of the two particles together is different from either particle by itself. The combined rate of a small and a large particle is slower than two large particles and faster than two small particles. Formulations of the invention are comprised of two or more groups of particles having a diameter of 2 to 40 microns and with 100 or more particles per group. The different groups of particles may include the same or different numbers of particles.

A particle with a large available surface area has a more rapid dissolution rate that a particle with a small available surface area. However, assuming the same total volume in two groups of particles the group of smaller particles has a faster dissolution rate than the group of larger particles because the group of smaller particles will have a larger available surface area than the group of larger particles.

It is often desirable to deliver a predetermined amount of compound (such as a drug) to a system (such as a human) at a rate which maintains the compound in the system at a desired level over a desired period of time. When the total amount (weight and volume) is fixed the rate of dissolution is dictated by the available surface area. One spherical particle with a given total volume will present approximately half the surface area as ten particles with the same combined volume as the one particle.

Each time the number of particles is increased by a multiple of ten (and the combined volume remains constant) the total available surface area approximately doubles (see Table 1). The following provides specific examples of how the total available surface area increases as the same total volume (e.g. a drug) is included in larger numbers of spheres.

Figure 4:
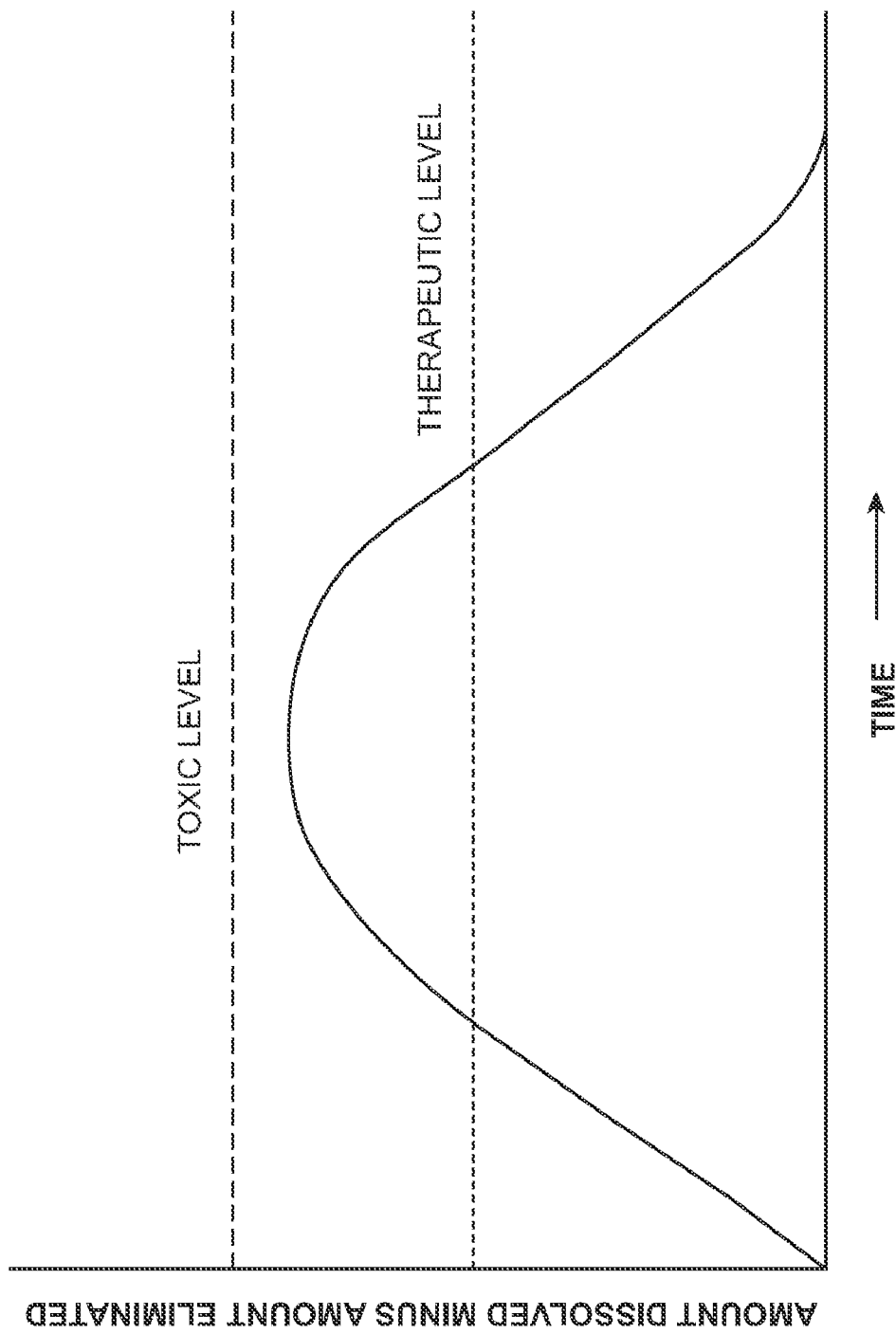
FIG. 4 is a schematic graph of time versus (amount of a compound dissolved minus the amount eliminated) for a single particle or group to substantially identical particles.

Formulations and/or devices coated with a formulation of the invention may include some antimicrobial by itself (no polymer sphere) such as an antibiotic for immediate release to provide a fast antimicrobial effect in the surrounding area. Further, greater numbers of groups of different particles can increase the duration time the drug is released and decrease changes in the concentration of the drug in the surrounding areas over time. Further, the multiple groups can be effective in keeping the concentration in the desired range—high enough to be therapeutic but low enough so as to not be toxic. Thus, 2 or more, 3 or more, 4 or more or 5 or more groups can be used to maintain the desired therapeutic level over time—see FIGS. 4, 5 and 6.

Specifics of Particle Sizes

Assuming a packet of formulation will contain a total volume of 2 cubic centimeters the size a single sphere which will hold a 2 cc volume can be readily calculated using the formula for the volume of a sphere as follows:

Volume of a sphere=$(4/3)\pi r^3$ if the volume of a sphere is 2 cc then $2\ cc=(4/3)\pi r^3$ $2=(4/3)3.14159 r^3$ $2=4.1887867 r^3$ $0.477645=r^3$ $0.781592\ cm=r$ $r=7{,}815$ micrometers diameter=$d=2r=15{,}630$ micrometers The formula for the surface area of a sphere is $4\pi r^2$. Because "r" was found to be 0.781592 cm the surface area=$4(3.14159)(0.781592)=9.8217\ cm^2$.

The formula for the volume of a sphere can be readily modified to determine the volume of any number of spheres "n" needed to make a total volume of 2 cubic centimeters.

$2\ cc=n(4/3)\pi r^3$

This formula was solved above for "n" equals "1" and can be solved for any "n." For example, when "n" is 10 the formula becomes $2\ cc=10(4/3)\pi r^3$ $2\ cc=10(4/3)3.14159 r^3$ $2\ cc=41.887867 r^3$ $0.0477645=r^3$ $0.362783\ cm=r$ $r=3627$ micrometers $d=7254$ micrometers The volume of each sphere is 0.2 cm$^3$ and the surface area of each sphere is 1.65388 cm$^2$. Thus, the total volume of the 10 spheres remains the same (i.e. 2 cc) but the surface area of all 10 spheres is 16.5 cm$^2$ as compared to 9.8217 cm$^2$ when "n" was one.

When "n" equals 100 the radius "r" can be solved for and found to be 0.1684 cm with the volume of each of the 100 spheres being 0.02 cm$^3$. The surface area of each sphere is 0.3563 cm$^2$ and the combined surface area of all 100 spheres is 35.63 cm$^2$—the combined volume remains the same at 2 cm$^3$. The equations for the surface area and volume can be used to solve for the radius "r" and diameter "d" of any number of spheres "n" which equal a total volume of 2 cm$^3$ and the results are provided below.

TABLE 1

| | Total volume is 2 cm$^3$ | | | |
|---|---|---|---|---|
| N | r(micro meters) | D | Surface area (cm$^2$) | Surface Area Volume (cm$^{-1}$) |
| 1 | 7815 | 15,630 | 9.8217 | 4.91085 |
| 10 | 3627 | 7,254 | 16.5 | 8.25 |
| 100 | 1684 | 3,378 | 35.63 | 17.815 |
| 1,000 | 781 | 1,562 | 76.766 | 38.383 |
| 10,000 | 362 | 724 | 165 | 82.5 |
| 100,000 | 168 | 336 | 356 | 178 |
| 1,000,000 | 78 | 156 | 768 | 384 |
| 10,000,000 | 36 | 72 | 1,653 | 826.5 |
| 100,000,000 | 16.8 | 33.6 | 3,563 | 1781.5 |
| 1,000,000,000 | 7.8 | 15.6 | 7,677 | 3838.5 |
| 10,000,000,000 | 3.6 | 7.2 | 16,539 | 8269.5 |
| 100,000,000,000 | 1.6 | 3.2 | 35,631 | 17815.5 |

From the above it can be seen that when "n" is increased by a factor of 10 and total combined volume is maintained constant at 2.0 and the combined surface area of all of the spheres increases by approximately a factor of 2 for each increase of 10× for n.

Although the surface area approximately doubles as "n" increases by a factor of ten the absolute effect of the doubling is small when "n" is increased from 1 to 10 to 100. Specifically, the increase in surface area from 9.8 to 16.5 is only an increase of 6.7 cm$^2$ and from 16.5 to 35.6 is only an increase of 19.1 cm$^2$. However, when "n" increases from $10^9$ to $10^{10}$ the surface area increases from 7677 to 16,539 resulting in an increase of 8,862 cm$^2$. When "n" increases from $10^{10}$ to $10^{11}$ the surface area increases from 16,539 to 35,631 resulting in an increase of 18,992 cm$^2$.

However, this differential in surface area between groups will be less when the total volume is less. This differential is based on a total volume of 2 cm$^3$ which is a large dose. The dose may be 1 cm³, 0.1 cm³, 0.01 cm³, 0.001 cm³ or less. With smaller volumes the total surface area differential between groups will be less.

For "n" at the extremes of the calculations provided above the gross increase in surface area is as follows:

TABLE 2

| N | gross increase in surface area (cm²) |
|---|---|
| 1 to 10 | 6.7 |
| 10 to 100 | 19.1 |
| $10^9$ to $10^{10}$ | 8,8863 |
| $10^{10}$ to $10^{11}$ | 18,992 |

The larger the available surface area the faster the rate of dissolution of the solute drug assuming the solvent is not saturated. In nearly all situations the solute drug will only be administered to the surrounding environment of the solvent (e.g. tissue such as bone) in relatively small amounts. Accordingly, the solvent never approaches saturation and the circulatory systems aids in refreshing the solvent over time.

Formulations of the invention are described and claimed here and such formulations may have two, three or a plurality of different groups of particles therein. The formulation suspension may be created where a first group has a first surface area and a second group has 1,000 square centimeters or more surface area than the first group or e.g. 2,000 or more; 5,000 or more; or 10,000 or more square centimeters of surface area per 0.1 cm³ of total volume per group of particles more than the surface area of the first group. Formulations of suspensions of particles may be created whereby a plurality of different groups are present and the total surface area of any one group different from the total surface area of any other group by a desired amount e.g. 1,000; 2,000; 3,000; 4,000; 5,000; and 10,000 or more square centimeters of surface area per 0.1 cm³ of total volume per group of particles.

Using data such as generated in Table 1 and the results of Table 2 a formulation of the invention can be created which provides a desired release profile. The desired release profile can be understood by reference to FIG. 7 which is a schematic diagram showing areas where a given concentration of antibiotic might be obtained over time with different drug delivery mechanisms. The square marked "gentamicin cement" shows that levels are maintained over a relatively long period of time. Due to maintaining these levels over long periods the bacteria may develop resistance to the antibiotic which is, of course, an undesirable result. Referring to the area 2 labeled as systemic gentamicin it can be seen that the antibiotic does not stay over a long period of time in order to develop antibiotic resistance. However, when delivered systemically the dose is generally subtherapeutic. When very high doses are given systemically the result may be some type of adverse toxic event including loss of hearing.

Within the area 3 marked "gentamicin powder" it can be seem that high levels are obtained and they are not generally obtained over a long period of time avoiding antibiotic resistance. However, the levels are so high that they may be toxic to the surrounding tissue and in particular inhibit bone growth. This is particularly disadvantageous when the patient has suffered bone damage and it is desirable to have the bone heal as quickly as possible. Thus, the area designated 3 shows that the antibiotic has reached a toxic level. It can be seen that the area 4 which is labeled "controlled release gentamicin microspheres" provides the desired release profile. Within this area the concentration of the antibiotic is therapeutic. However, it is not so high as to be toxic. Further, the therapeutic level is not maintained over a sufficiently long period of time so as to develop antibiotic resistance.

It will be understood that the formulation and amount of drug can vary depending on the particular drug and the polymer used. Further, the shape and size of the particles will effect the dissolution time as well as the particle configuration. More particularly, the particle may be comprised of polymer intermixed with the drug or have the drug encapsulated within a polymer. There will also be some variation depending on the patient in that patient's with poor circulation provide a different environment for the particles as compared to patient's with normal circulation.

The solvent is the surrounding environment which can be any area where the drug is delivered including the blood, body fluids, tissue including bone. The solvent or surrounding environment into which the drug is administered can be assumed to be known within a given environment (e.g. bone tissue or blood) in a given species of animal (e.g. human). Thus, the unknown that remains is the rate of dissolution of a particle of known size in a given solvent. After calculating the rate of release "R" (weight or volume dissolved per unit of time) for a known particle size the rate of dissolution of other particle sizes with different available surface areas can be calculated. Assuming all the particles of a group of particles are spherical and also assuming that the particles in a given group of particles all have substantially the same size (available surface area), the rate of dissolution of a group of particles can be readily determined. Using this information a formulation can be created with different groups or types of particles wherein each group of particles has a known drug release profile within the environment the formulation is delivered to. The formulation preferably comprises a number of different groups which release drug at different rates and/or times and provide a desired drug release profile, e.g. substantially constant levels in the surrounding area over a therapeutically effective time period.

Calculations are provided below in Tables 3, 4 and 5 respectively for total volumes of 1 cm³, 0.5 cm³ and 0.1 cm³ which are volume sizes that might be used for typical dosages of orally administered pharmaceutically active compounds.

TABLE 3

| Total volume is 1 cm³ | | | | |
|---|---|---|---|---|
| number of spheres | Radius (micrometers) | Diameter (micrometers) | Surface area (cm²) | Surface area Volume (cm⁻¹) |
| 1 | 6203.5 | 12407.0 | 4.84 | 4.8 |
| 10 | 2879.4 | 5758.8 | 10.42 | 10.4 |
| 100 | 1336.5 | 2673.0 | 22.45 | 22.4 |
| 1,000 | 620.4 | 1240.7 | 48.36 | 48.4 |
| 10,000 | 287.9 | 575.9 | 104.19 | 104.2 |
| 100,000 | 133.7 | 267.3 | 224.47 | 224.5 |
| 1,000,000 | 62.0 | 124.1 | 483.60 | 483.6 |
| 10,000,000 | 28.8 | 57.6 | 1041.88 | 1041.9 |

TABLE 3-continued

Total volume is 1 cm³

| number of spheres | Radius (micrometers) | Diameter (micrometers) | Surface area (cm²) | Surface area Volume (cm⁻¹) |
|---|---|---|---|---|
| 100,000,000 | 13.4 | 26.7 | 2244.66 | 2244.7 |
| 1,000,000,000 | 6.2 | 12.4 | 4835.98 | 4836.0 |
| 10,000,000,000 | 2.9 | 5.8 | 10418.79 | 10418.8 |
| 100,000,000,000 | 1.3 | 2.7 | 22446.61 | 22446.6 |

TABLE 4

Total volume is 0.5 cm³

| number of spheres | Radius (micrometers) | diameter (micrometers) | Surface area (cm2) | Surface area Volume |
|---|---|---|---|---|
| 1 | 4923.7 | 9847.5 | 3.05 | 6.1 |
| 10 | 2285.4 | 4570.8 | 6.56 | 13.1 |
| 100 | 1060.8 | 2121.6 | 14.14 | 28.3 |
| 1,000 | 492.4 | 984.7 | 30.46 | 60.9 |
| 10,000 | 228.5 | 457.1 | 65.63 | 131.3 |
| 100,000 | 106.1 | 212.2 | 141.40 | 282.8 |
| 1,000,000 | 49.2 | 98.5 | 304.65 | 609.3 |
| 10,000,000 | 22.9 | 45.7 | 656.34 | 1312.7 |
| 100,000,000 | 10.6 | 21.2 | 1414.05 | 2828.1 |
| 1,000,000,000 | 4.9 | 9.8 | 3046.47 | 6092.9 |
| 10,000,000,000 | 2.3 | 4.6 | 6563.43 | 13126.9 |
| 100,000,000,000 | 1.1 | 2.1 | 14140.48 | 28281.0 |

TABLE 5

Total volume is 0.1 cm³

| number of spheres | radius (micrometers) | Diameter (micrometers) | Surface area (cm2) | Surface area Volume |
|---|---|---|---|---|
| 1 | 2879.4 | 5758.8 | 1.04 | 10.4 |
| 10 | 1336.5 | 2673.0 | 2.24 | 22.4 |
| 100 | 620.4 | 1240.7 | 4.84 | 48.4 |
| 1,000 | 287.9 | 575.9 | 10.42 | 104.2 |
| 10,000 | 133.7 | 267.3 | 22.45 | 224.5 |
| 100,000 | 62.0 | 124.1 | 48.36 | 483.6 |
| 1,000,000 | 28.8 | 57.6 | 104.19 | 1041.9 |
| 10,000,000 | 13.4 | 26.7 | 224.47 | 2244.7 |
| 100,000,000 | 6.2 | 12.4 | 483.60 | 4836.0 |
| 1,000,000,000 | 2.9 | 5.8 | 1041.88 | 10418.8 |
| 10,000,000,000 | 1.3 | 2.7 | 2244.66 | 22446.6 |
| 100,000,000,000 | 0.6 | 1.2 | 4835.98 | 48359.8 |

Particle Formation Methodology

Particles and coated particles can be produced via any available technology. Referring to FIG. 1, cylindrical tube 1 is shown in fluid connection with a liquid source 2 which can supply liquid 3 to the tube 1. The liquid 3 exits the tube 1 from an exit opening which can be any configuration but is preferably circular and has a diameter D. The liquid 3 exits the opening 4 and forms a stream which breaks into segments 5 and eventually forms partial spheres 6 and then spheres 7 which are substantially equal in size and shape. The spheres 7 could be used in creating a group of particles for attachment to a device such as a surgical screw. Different size spheres from different sized tubes 1 could create different groups of spheres as needed for a desired dissolution profile.

The processing of FIG. 1 can stop at the formation of the particles 7. However, in order to attempt to obtain a dissolution profile which achieves a longer steady state level of the desired compound a coating is often used. The coating source 8 creates a spray 9 of a coating material which is brought into contact with and sticks to particles 10, 11 and 12 often in different amounts. Further, two particles 13 may become coated together or three or more particles 14 may become coated together.

The result is a random mixture of particles coated to different degrees and combined with different numbers of other particles. Coated particles of this type could be used if they provide the desired level of drug at the target site over the desired period of time. The coating material can be mixed with rather than sprayed on the particles and a similar random mixture of coated particles and coated groups of particles will result. The random mixture has some advantages. It can provide a greater range of release rates than a single type of particle. The greater range of release rates may provide a release profile which is desirable. However, a degree of trial and error is required in producing a desired release profile. Further, great care must be taken once the desired profile is obtained in repeating all preparation steps precisely from batch to batch. Otherwise, each new batch of formulation produced will have a different release profile.

The process for producing particles 7 as shown in FIG. 1 has yet another disadvantage or limitation. Specifically, the diameter D of the tube 1 dictates that the diameter of the particles 7 formed will be approximately D×1.89 (Rayleigh, "On the instability of jets", Proc. London Math. Soc., 4-13, 1878). Thus, when attempting to make very small particles (e.g. less than 20 micrometers) the inside diameter of the tube 1 must be very small. Not only is it difficult to manufacture tubes with such a small diameter but the narrower tubes tend to clog easily. These problems can be solved by using a different technology for producing particles and coated particles as shown in FIGS. 2 and 3.

Figure 2:
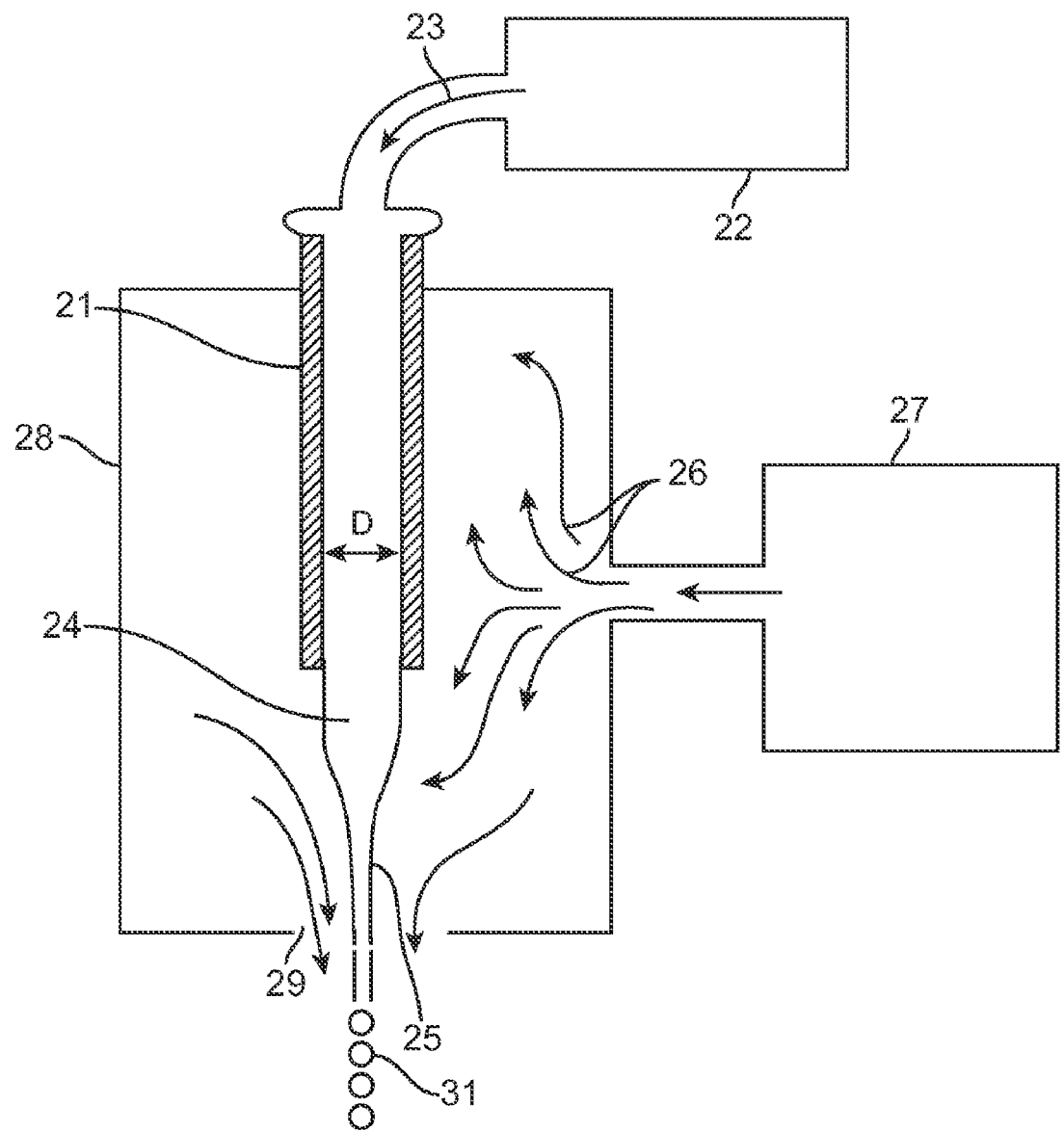
FIG. 2 is a schematic view of an embodiment of an extrusion device used to create spherical particles of substantial uniform size and spherical shape.

FIG. 2 shows a tube 21 supplied by a liquid source 22. The liquid 23 flows out of the exit 24. The liquid 23 stream is focused to a narrowed stable jet 25 by a gas 26 provided by the gas source 27 flowing into a pressure chamber 28 and out of an exit orifice 29. The jet 25 disassociates into segments 30 which form spheres 31 in the same manner in which the stream of liquid 3 forms the spheres 7 shown in FIG. 1. However, the spheres 31 have a diameter which is 1.89× the diameter $D_j$ of the jet and not 1.89× the diameter D of the tube 21. The diameter of the jet 25 ($D_j$) is substantially smaller than the diameter D of the tube 21. Thus, the system of FIG. 2 can be used to make very small particles as compared to the system of FIG. 1 without clogging the exit 24 of the tube 21 because the diameter D of the tube 21 can remain large—and without clogging the exit orifice 29 of the pressure chamber 28 because the jet 25 exits the orifice 29 surrounded by the gas 26.

The particles 31 can be coated using a spray on coating as shown in FIG. 1. However, similar problems occur as described above with reference to FIG. 1. The particles 31 can be used without any coating. Groups of particles can be combined to provide a desired dissolution profile. The small size of the particles provides certain advantages as shown in Tables 1-5. Particles in a size range of 1-20 micrometers can not be easily produced in a system as shown in FIG. 1 and particles in this size range provide the greatest differences in surface areas—see Tables 1-5 and Table 2 in particular. However, the particles themselves (without a coating) are limited in terms of the dissolution profile they can produce particularly when the total volume of the particles in a formulation is limited. Thus, a coating is preferred and a preferred means of obtaining such is shown in FIG. 3.

Figure 3:
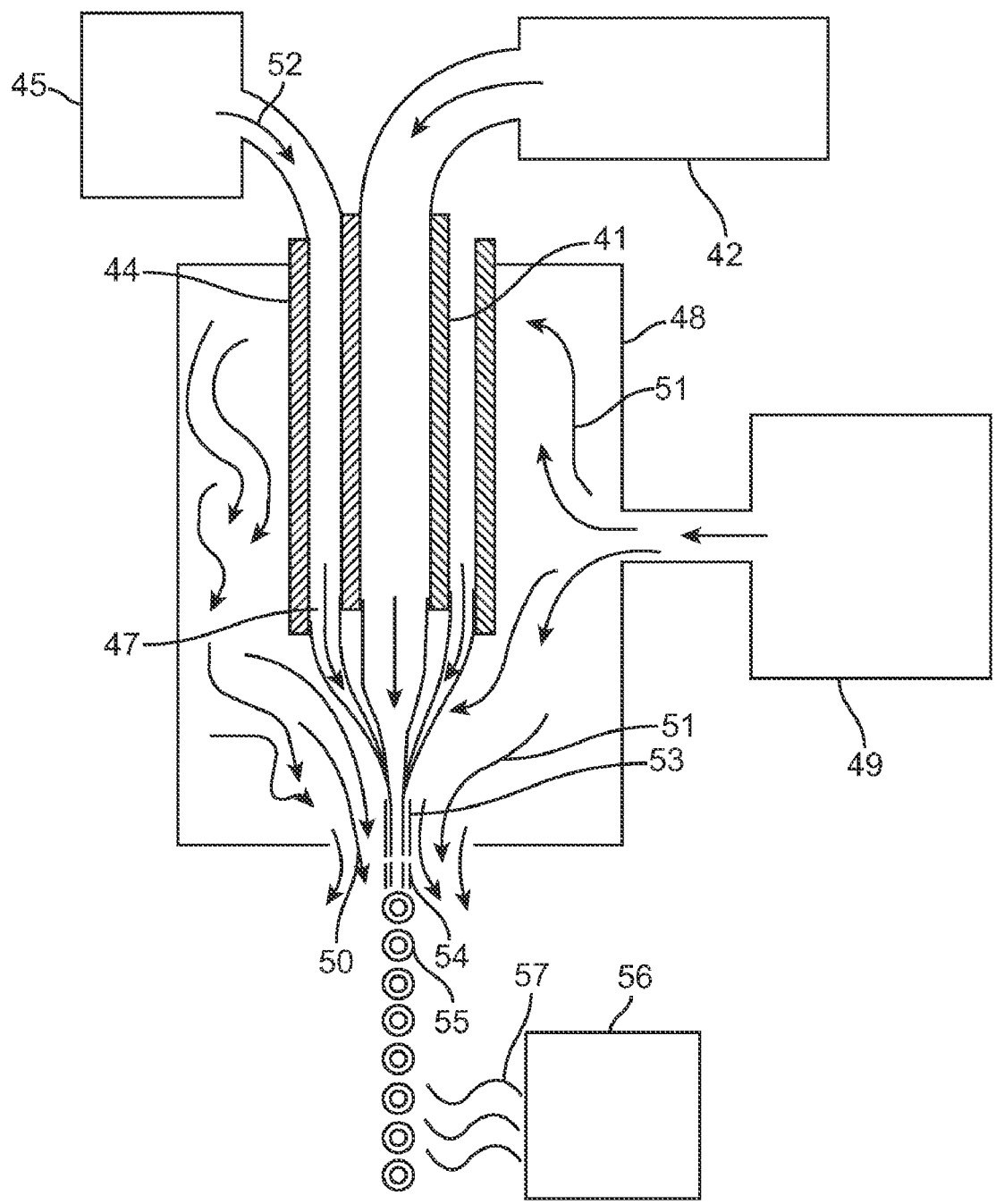
FIG. 3 is a schematic view of an embodiment of an extrusion device used to create spherical coated particles of substantial uniform size and spherical shape.

The system schematically shown in FIG. 3 includes a tube 41 in fluid connection with a liquid source 42 which supplies liquid 43 to the cylindrical channel of the tube 41. A tube 44 is concentrically positioned around the tube 41 and is in fluid connection with a coating source 45. The exit opening 46 of the tube 41 and the exit opening 47 of the tube 44 are both positioned inside of a pressure chamber 48. The chamber 48 is in fluid connection with the gas source 49 which flows out of the exit orifice 50 of the chamber 48. The gas 51 focuses the streams of liquid 43 and coating 52 into a stable jet 53. The jet 53 disassociates into segmented streams 54 of liquid 43 concentrically surrounded by coating 52. The segmented streams 53 form spheres 55. The spheres 55 are comprised of a liquid 43 center surrounded by a polymeric (e.g. PLGA) coating 52. The spheres 55 are preferably very small, e.g. a diameter of less than 50 µm, preferably less than 20 µm and more preferably about 10 µm. The smaller the particles the more readily evaporation will take place which will cure or solidify the coating 52.

An energy source 56 may be used to direct energy 57 onto the particles 55 to enhance the rate of curing, hardening, evaporation, etc. The energy 57 may be any type of energy including heat, forced air, I.R. or U.V. light etc. alone or in combination. Some polymer materials are designed to be cured using a particular frequency of light. The light can be directed, focused and/or intensified using lenses, mirrors and the like to obtain a desired result. The particles 55 could be produced and dispersed in a biocompatible gel and applied to bone and/or an orthopedic implant.

The coated particles 55 can include any liquid 43 coated with any coating material 52. However, in accordance with the present invention it is preferable that the liquid 43 be comprised of a pharmaceutically active drug which is preferably an antimicrobial and more preferably an antibiotic. Further, the coating material can be comprised of any type of material which can be cured, dried or fixed in any fashion in order to form an outer spherical coating around the center. However, it is preferable that the coating material be comprised of a polymer material and more preferable if the polymer material is quickly and readily curable and is a material which is commonly accepted as useful as a carried material in controlled release formulations used in pharmaceutical applications. A number of such polymer materials are disclosed within the patents and publications described below.

U.S. Pat. No. 3,773,919 describes creating slow release formulations producing a steady release of drug in the bloodstream by employing polylactide-drug mixtures in the dosage form. The inventors describe using a chemical based microencapsulation procedure for forming precipitates of the polylactide-drug mixtures suitable for injection. They discuss many potential applications for their invention including the administration of morphine.

U.S. Pat. No. 4,942,035 describes using PLGA polymer as an excipient allowing formulations to be created to facilitate the controlled release of polypeptide active drugs into solutions.

U.S. Pat. No. 5,514,380 describes modifying the crosslinking in PLGA polymer in order to obtain more controllable release profiles.

U.S. Pat. No. 5,543,158 describes potential benefits of using PLGA polymer with pharmaceutically active drug to create particles in a very small size range to minimize incorporation of the injected formulation into the patient's macrophages which would result in inactivation of the drug.

U.S. Pat. No. 5,650,173 describes an emulsion system for creating particles of PGLA and active drug suitable for injection.

U.S. Pat. No. 5,654,008 describes a technique for combining PLGA and active drug into microparticles suitable for injection by using an emulsion system created using a static mixer.

U.S. Pat. No. 5,759,583 describes using a quaternary ammonium surfactant as an excipient to facilitate the creation of PLGA drug combinations suitable for injection to create a controlled release formulation.

U.S. Pat. No. 5,912,015 describes using metal cations as release modulators in the injectable drug formulation comprising PLGA and active drug.

U.S. Pat. No. 5,916,598 describes using emulsion systems and solvent extraction techniques as tools for creating microparticles comprised of PLGA and active drug for sustained release formulations.

U.S. Pat. No. 6,254,890 describes using PLGA to create sustained release formulations containing nucleic acids.

Previous approaches for combining PLGA with active drug to create such controlled release formulations relied on chemical techniques for creating microparticles suitable for injection. These techniques have focused on the use of solvent systems to produce emulsions resulting in the creation of a precipitate of crystalline microparticle in an approximate size range suitable for injection. Other systems involve removing solvents used during the fabrication process. The US FDA as well as international drug regulatory authorities have drafted regulations strictly limiting the amount of residual solvent acceptable in marketed pharmaceutical preparations (ICH Harmonized Tripartite Guideline Q3C Impurities: "Guidelines for Residual Solvents").

Additional discussion of categories of systems for controlled release may be found in Agis F. Kydonieus, *Controlled Release Technologies: Methods, Theory and Applications*, 1980 (CRC Press, Inc.).

Controlled release drug delivery systems may also be categorized under their basic technology areas, including, but not limited to, rate-preprogrammed drug delivery systems, activation-modulated drug delivery systems, feedback-regulated drug delivery systems, and site-targeting drug delivery systems.

In rate-preprogrammed drug delivery systems, release of drug molecules from the delivery systems is "preprogrammed" at specific rate profiles. This may be accomplished by system design, which controls the molecular diffusion of drug molecules in and/or across the barrier medium within or surrounding the delivery system. Fick's laws of diffusion are often followed.

In activation-modulated drug delivery systems, release of drug molecules from the delivery systems is activated by some physical, chemical or biochemical processes and/or facilitated by the energy supplied externally. The rate of drug release is then controlled by regulating the process applied, or energy input.

In feedback-regulated drug delivery systems, release of drug molecules from the delivery systems may be activated by a triggering event, such as a biochemical substance, in the body. The rate of drug release is then controlled by the concentration of triggering agent detected by a sensor in the feedback regulated mechanism.

In a site-targeting controlled-release drug delivery system, the drug delivery system targets the active molecule to a specific site or target tissue or cell. This may be accomplished, for example, by a conjugate including a site specific targeting moiety that leads the drug delivery system to the vicinity of a target tissue (or cell), a solubilizer that enables the drug delivery system to be transported to and preferentially taken up by a target tissue, and a drug moiety that is covalently bonded to the polymer backbone through a spacer and contains a cleavable group that can be cleaved only by a specific enzyme at the target tissue.

Another controlled release dosage form is a complex between an ion exchange resin and the lipoates. Ion exchange resin-drug complexes have been used to formulate sustained-release products of acidic and basic drugs. In one preferable embodiment, a polymeric film coating is provided to the ion exchange resin-drug complex particles, making drug release from these particles diffusion controlled. See Y. Raghunathan et al., *Sustained-released drug delivery system I: Coded ion-exchange resin systems for phenylpropanolamine and other drugs*, J. Pharm. Sciences 70: 379-384 (1981).

Injectable micro spheres are another controlled release dosage form. Injectable micro spheres may be prepared by non-aqueous phase separation techniques, and spray-drying techniques. Micro spheres may be prepared using polylactic acid or copoly(lactic/glycolic acid). Shigeyuki Takada, *Utilization of an Amorphous Form of a Water-Soluble GPIIb/IIIa Antagonist for Controlled Release From Biodegradable Micro spheres*, Pharm. Res. 14:1146-1150 (1997), and ethyl cellulose, Yoshiyuki Koida, *Studies on Dissolution Mechanism of Drugs from Ethyl Cellulose Microcapsules*, Chem. Pharm. Bull. 35:1538-1545 (1987).

To form a coated particle 55 the liquid 43 is forced through the channel of the tube 41. The liquid is preferably a relatively high concentration of a drug such as an antibiotic in either an aqueous or alcohol based solvent or other solvent which will quickly evaporate (e.g. ether). The exit opening 46 of the tube 41 and the exit opening 47 of the tube 44 are both positioned inside the pressure chamber 48. The coating material 52 is initially in a liquid form and is forced through the exit opening 46 of the tube 44 which is positioned concentrically around the tube 41 in a manner which causes a stream of the liquid coating material to be expelled from the opening 47 at substantially the same velocity as the liquid 43 is forced from the opening 46 of the tube 41. Accordingly, the stream of the coating material is concentrically positioned around the stream of the center liquid 43. The streams exit the openings of the two concentrically positioned tubes as a single combined stream which then disassociates into segments streams 53 which segments form the cooled spheres 55.

In order for the spheres to be made small it is effective to use the gas from the gas source 49 forced into the pressure chamber 48 in a manner which causes the gas to exit the pressure chamber 48 downstream of the concentrically positioned streams exiting the tubes 41 and 44. It is preferable for the density of the liquid 43 to be substantially the same as the liquid of the coating 52. This allows the gas from the gas source 49 to focus the concentrically positioned streams into a stable unified jet which flows out of the chamber 48 breaking up into segments and thereafter forming the spherical coated particles 55 of the coating material surrounding the center of pharmaceutically active drug.

In accordance with the invention the gas from the gas source forms the stable jet and the diameter of the jet is substantially smaller than would be the case if the gas were not focusing the streams exiting the tubes 41 and 44. The diameter of the jet is defined by the following formula:

$$d_j \cong \left(\frac{8\rho_1}{\pi^2 \Delta P_g}\right)^{1/4} Q^{1/2}$$

wherein $d_j$ is the diameter of the stable unified jet, ≅ indicates approximately equally to where an acceptable margin of error is ±10%, $\rho_1$ is the average density of the liquid of the jet and $\Delta P_g$ is change in gas pressure of gas surrounding the stream at a given point A at the exit and Q is the total flow rate of the stable unified jet.

By using the technology described above and shown in FIGS. 2 and 3 it is possible to form very small and very uniform particles. The particles may be of any size but are preferably in less than 100 micrometers in diameter, more preferably less than 50 micrometers in diameter and still more preferably less than 20 micrometers in diameter. The technology described above and shown in FIGS. 2 and 3 is capable of producing particles which are as small as approximately 1 micrometer in diameter and preferred devices of the invention will include particles which have a diameter of approximately 10 micrometers. The sphere forming technology can produce particles which are substantially identical in shape (spherical) and substantially identical in size ±10% variation in the particle diameter, more preferably ±3% and still more preferably ±1% variation in particle diameter where the particle may have a diameter as small as 1 μm or more or as large as 100 μm or more.

Those skilled in the art will understand that in addition to the tubes 41 and 44 a plurality of additional concentrically positioned tubes may be added to the system. This would make it possible to add additional coating materials or include additional active components surrounded by outer shells of coating material. An out coating of adhesive could be added so that the particles 55 have an adhesive thereon and adhere to an orthopedic implant and/or to bone. Those skilled in the art will understand that the system works best when the Weber Number is in a range of from about 1 to about 40 wherein the Weber Number is defined by the following equation:

$$We = \frac{\rho_g V_g^2 d}{\gamma}$$

wherein the $\rho_g$ is the density of the gas, d is the diameter of the stable microjet, $\gamma$ is the liquid-gas surface tension and $V_g^2$ is the velocity of the gas squared. More preferably the Weber number is in a range of about 5 to about 25.

Further, those skilled in the art will understand that it is preferable for the Ohnesorge number to be less than 1, wherein the Ohnesorge number (Oh) is defined by $$Oh = \frac{\mu_1}{(\rho_l \gamma d)^{1/2}}$$

wherein $\mu_1$ is the velocity of the liquid, $\rho_1$ is the density of the liquid and d is the diameter of the stable capillary microjet.

Those skilled in the art will also understand that the method for producing particles and coated particles as described above is best carried out when the difference in the pressure between the pressure chamber exit orifice is equal to or less than 20 times the surface tension of the liquid comprising the coating material with the gas, divided by the radius of the stable unified jet. Details relating to the technology are described within issued U.S. Pat. No. 6,234,402 issued May 22, 2001 and incorporated herein by reference. Those skilled in the art will understand that some adjustments may be made in the density and velocity of the different fluids and gases used in order to obtain the desired result in terms of the fluid—fluid interfaces including the particle interface between the coating material and the inner liquid material as well as the stable interface between the gas and the coating material. It is desirable to obtain the stable microjet stream which has substantially no aberrations or perturbations in the stream making it possible for the stream to disassociate into very uniform size and shaped particles. The two related systems shown in FIGS. 2 and 3 make it possible to maintain a stable liquid-gas interface between the outer surface of the liquid or coating material and the gas thereby forming a stable jet which is focused on the exit orifice of the pressure chamber resulting in particles which have very small deviation in terms of diameter from one particle to the next. It is also possible to create hollow particles and to reverse the positioning of the different fluids. For examples, the center tube can be used to supply gas whereas the pressure chamber can be used to supply a liquid. The technology for such is described within issued U.S. Pat. No. 6,196,525 issued Mar. 6, 2001 which patent along with other patents cited herein is incorporated in its entirety.

Dissolution Profiles

When any particle dissolves in any solvent the amount of solute in the solution increases over time. However, some solvents are present in systems where the portion of the dissolving solute is being removed from the solution. This could take place in a chemical reaction where a portion of the dissolved solute reacts with another components present in the system. However, the most typical situation is where a drug present in an area and diffuses away from that area which subtracts solute drug from the surrounding area. In any such system the dissolution profile over time shows an increase followed by a steady state followed by a decrease as is shown by the solid line in FIG. 4. It is desirable to maintain the level of a drug above the therapeutic level shown by the line of short dashes but below a toxic level shown by the line of long dashes or level where addition drug provides no additional benefit. Maintaining the level of drug in a desired range for a significant period is difficult to obtain particularly when using a single type of particle.

Figure 5:
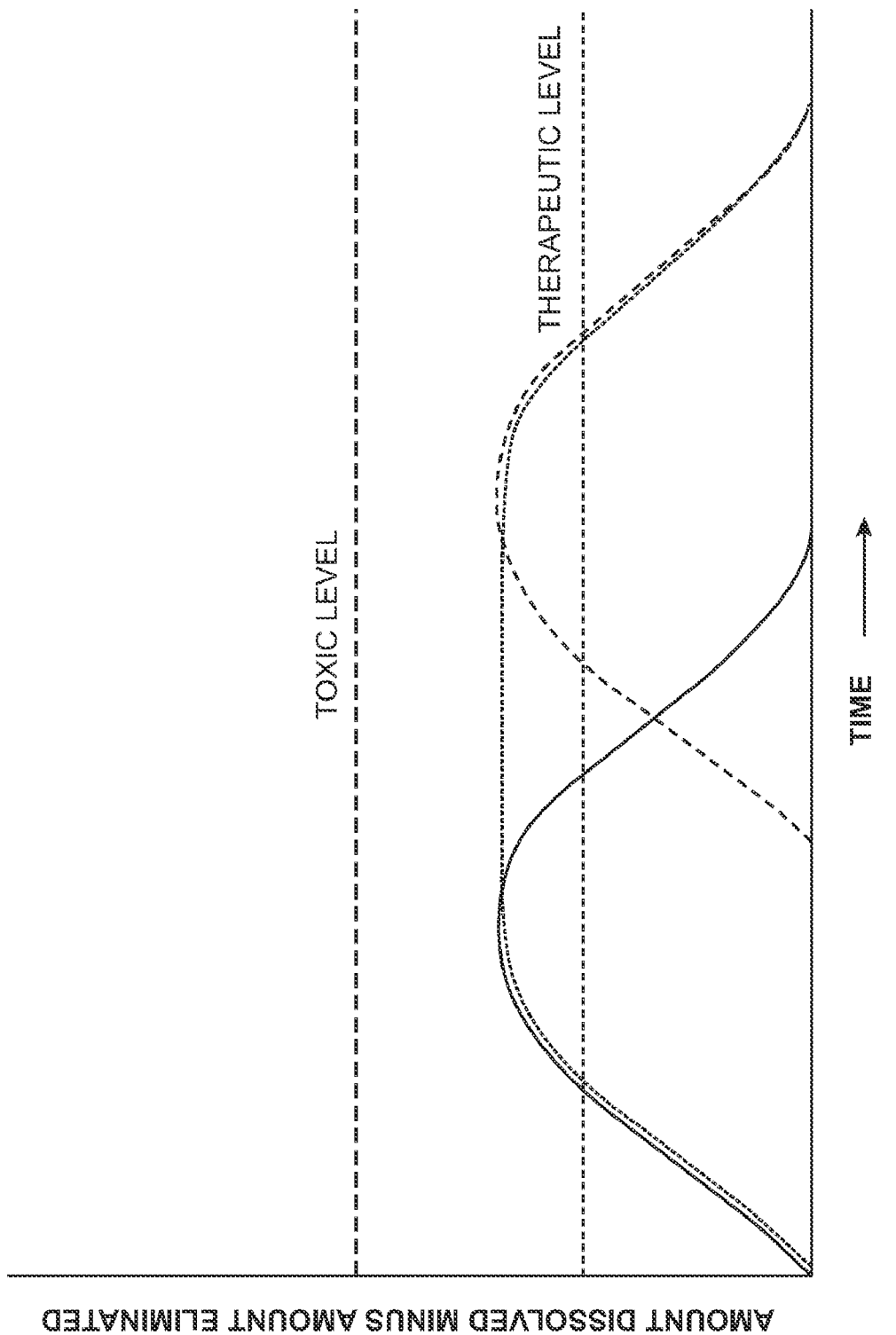
FIG. 5 is a schematic graph of time versus (amount of a compound dissolved minus the amount eliminated) for two different particles or two different groups of particles (solid and dashed lines) where the particles within a given group are substantially identical and also showing the combined effect of the two groups (dotted lines).
Figure 6:
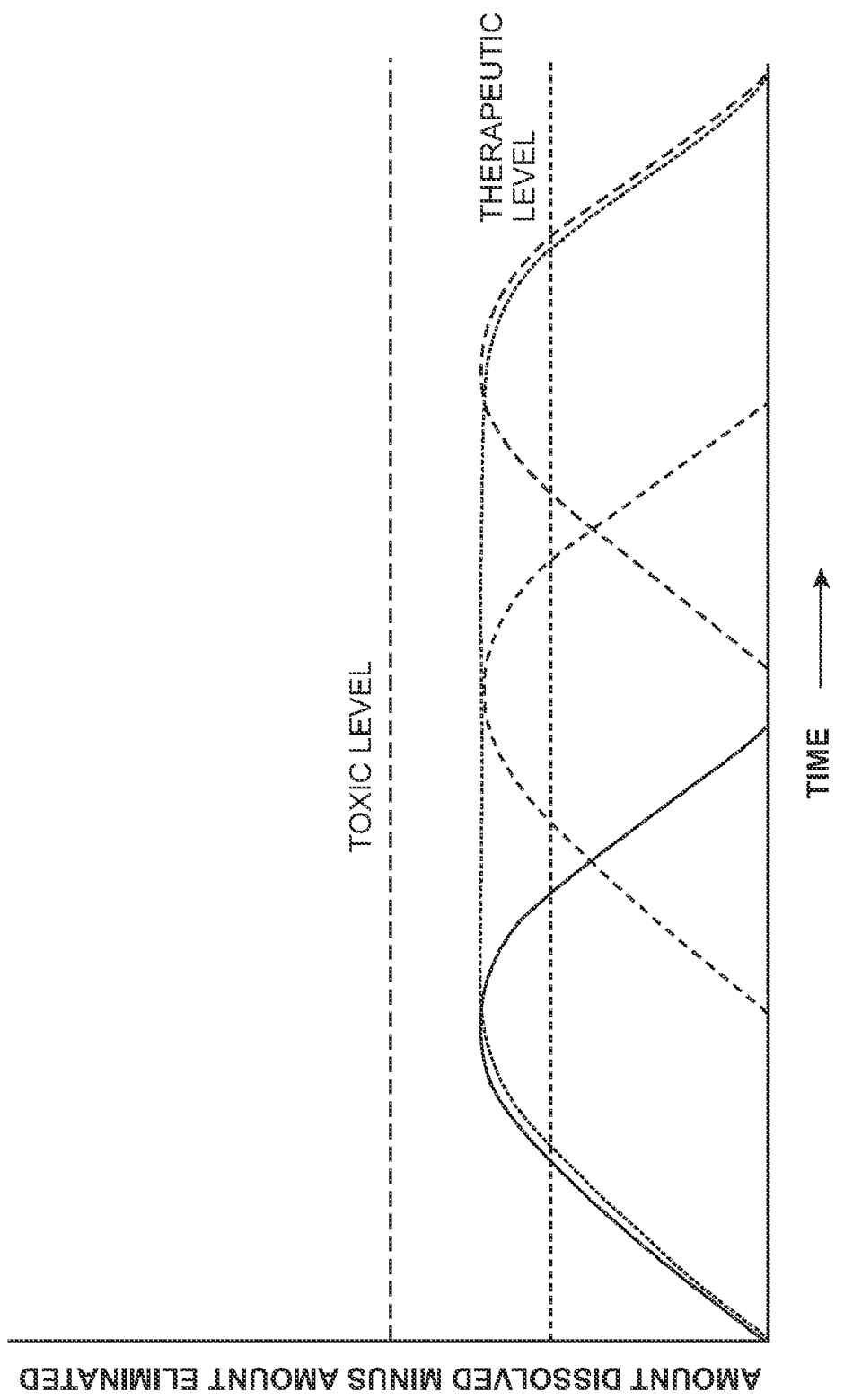
FIG. 6 is a schematic graph of time versus (amount of a compound dissolved minus the amount eliminated) for three different particles or three different groups of particles where the particles within a given group are substantially identical and also showing the combined effect of the three groups.

FIG. 5 shows how the therapeutic level can be maintained over a longer period of time using two different types of particles. In FIG. 5 the independent effect of a first type of particle is shown by the solid line. The dashed curve shows the independent effect of a second type of coated particle. The dotted curve shows the combined effect of the two types of particles. When the particle of the first type are completely dissolved and are being metabolized out of the system the coatings on the particle of the second type have dissolved and the rate of dissolution matches the rate at which all drug in the system is being diffused out of the desired area. Thus, a longer steady state period is maintained. This effect is further enhanced using three different types of particles as shown in FIG. 6.

Controlled release within the scope of this invention can be taken to mean any one of a number of extended release dosage forms. The following terms may be considered to be substantially equivalent to controlled release, for the purposes of the present invention: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, *Extended-Release Dosage Forms*, 1987 (CRC Press, Inc.).

There are corporations with specific expertise in drug delivery technologies including controlled release oral formulations such as Alza corporation and Elan. A search of patents, published patent applications and related publications will provide those skilled in the art reading this disclosure with significant possible controlled release technologies. Examples include the technologies disclosed in any of the U.S. Pat. No. 5,637,320 issued Jun. 10, 1997; U.S. Pat. No. 5,505,962 issued Apr. 9, 1996; U.S. Pat. No. 5,641,745 issued Jun. 24, 1997; and U.S. Pat. No. 5,641,515 issued Jun. 24, 1997. Although specific technologies are disclosed here and in these patents the invention is more general than any specific technology. This includes the discovery that by placing pharmaceutically active drug in a plurality of controlled release particle groups which maintain therapeutic levels (but not toxic levels) over periods of time which are longer as compared to quick release formulations, but shorter compared to bone cement, improved unexpected results are obtained.

Particles Formed Using Supercritical Fluid Precipitation

The devices, systems and methodology disclosed and described above in connection with FIGS. 2 and 3 can also be used in combination with supercritical fluid precipitation technology of the type described within U.S. Pat. No. 6,063,910 issued May 16, 2000; U.S. Pat. No. 5,766,637 issued Jun. 16, 1998; U.S. Pat. No. 6,228,394 issued May 8, 2001; and U.S. Pat. No. 6,095,134 issued Aug. 1, 2000 all of which are incorporated herein by reference in their entirety. Basically, the technology utilizes a supercritical fluid such as liquid $CO_2$ in order to form solid particles of a material such as a drug or a protein for use in a formulation.

Referring to FIG. 2 the gas source 27 could be replaced with a liquid $CO_2$ and the liquid $CO_2$ could become the focusing fluid. The liquid 23 supplied into the tube 21 could be any liquid comprised of any desired material. However, the liquid 23 would preferably be a liquid which included an active compound such as a drug which is dissolved within a solvent such as water and further combined with a solvent such as ethanol. The solvent liquid 23 is focused by the surrounding liquid 26 which may be $CO_2$. When the $CO_2$ exits the pressure chamber 28 via the orifice opening 29 the rapid evaporation draws the liquid water and ethanol away leaving dry particles 31.

Referring to FIG. 3 it would also be possible to use supercritical fluids in place of the coating 52 or in place of the gas 51. Those skilled in the art will recognize that a variety of different combinations of liquids, gases, solutions and supercritical fluids are possible using the systems as shown and described above with respect to FIGS. 2 and 3 particularly when taken in combination with the above-referenced patents which disclose basic technology used in the field of supercritical fluid precipitation.

Heterogenous Particle Formulations

A packet of formulation can be a disposable container of spheres with a group or plurality of groups of spheres in each packet. The packet may be a syringe which includes the particles in a liquid or a gel such as Florseal™. Alternatively, the packet may be a sealed container such as a foil packet holding an absorbable collagen sponge having the particles dispersed evenly therein. A first group of spherical particles is present wherein each particle of the first group has a same diameter as other particles in the group with a margin of error in terms of particle diameter size of approximately ±10% or less. The formulation may then include a second group of spherical particles wherein each particle of the second group has the same diameter as the other particles in the second group with a margin of error of about ±10% or less. The particles within the first group are different from the particles within the second group (e.g. see Table 1) and preferably have a difference in terms of the steady state levels which difference is sufficient to provide a longer steady state level of antimicrobial to the surrounding area than either of the groups by themselves. Preferably, the first group of particles and the second group of particles each comprise 100 or more particles, more preferably a 1,000 of more particles, and still more preferably 10,000 or more particles and may comprise $10^5$ to $10^{10}$ or more particles.

Although the heterogeneous groups of particles in a formulation can be produced using particle formation technology of various types the technology as described above with respect to FIGS. 2 and 3 are preferred in that they produce very uniform sized and shaped particles. Further, the particles may be solid spheres which may be produced using the technology as shown in FIG. 2. A formulation or device of the invention may include groups of particles wherein the particles are coated using the technology as shown within FIG. 3.

A formulation may include 3 or more groups of spherical particles wherein the particles within each group are the same relative to other particles in that group and are different between the groups. A formulation may comprise at least some particles which are not coated e.g. a first group of particles with no coating and a relatively small particle size. Thus, the first group of particles will provide for substantially immediate dissolution and release of all of the compound or drug which is present in the particles. This causes the drug to quickly reach a therapeutic level in the desired surrounding area. The remaining groups of particles are larger and include polymers and remain undissolved. When a known amount of time has passed diffusion will have removed from the surrounding area (e.g. the bone) a sufficient amount of the drug added by the first group such that the concentration of the drug in the surrounding area is beginning to decline. With this decline the second group of particles increase their dissolution to add drug to the surrounding area thereby gradually increasing the concentration via the second group of particles at a rate substantially corresponding to the rate at which drug from the first group of particles is being decreased and diffused out of the area. This is shown within the graph of FIG. 5. The process can be repeated several times with several different groups of particles and three different groups of particles are shown within the graph of FIG. 6. The groups may be included in a packet of formulation which may be a disposable, one use, syringe with a gel and the syringe, gel, and particles may be included in a kit. The kit may include another drug which compliments the drug in the particles.

In one embodiment of the invention an antimicrobial is dissolved in a solvent which may be water, ethanol or a combination of water and ethanol. The solution is saturated with drug and the saturated solution is then coated with a polymer material which can be quickly cured by the addition of energy or evaporation as shown within FIG. 3. Thus, a group of particles is formed wherein the particles are comprised of a liquid center which liquid is comprised of a saturated solution of drug and solvent in an outer core of polymer material which is substantially inert i.e. does not provide a pharmacological effect. Such particles are produced in a variety of different size ranges. Each size is used to produce a group of particles which, by itself, is sufficient to provide for therapeutic levels of a drug to a given area such as an area surrounding the implant. When the coating dissolves the liquid within the spheres, which is a liquid drug (e.g. a drug in an aqueous solution) is immediately released. When the drug has diffused away to the point of beginning to drop below therapeutic levels the next group of particles with a thicker coating have dissolved to the point where the drug within these particles is released raising the level of drug in the surrounding area. By including a plurality of different groups it is possible to maintain the therapeutic level of the drug over a long period of time e.g. 1 day, several days (2 to 6 days) or 72 hours±12 hours. Care should be taken to avoid developing resistant bacteria.

Those skilled in the art will recognize that variability in terms of the rate at which the polymer material dissolves can be changed by changing the composition of the polymer material as some materials will dissolve more quickly than others. Accordingly, the different groups of particles within the formulation may be particles which are all of the same size, but have different polymer materials. In one embodiment the composition of coating on one group of particles dissolves more rapidly than the coating composition on another group within the formulation.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Those skilled in the art will recognize that the technology described here can be provided to a number of different types of drugs and to heterogenous formulations of all different numbers of particle groups. However, here a specific example is described wherein the active drug is first included within particles which have no coating and thereafter are included within two additional groups of particles wherein the percent thickness of the spheres is varied.

|  | Sphere Diameter | | |
| --- | --- | --- | --- |
| Capsule Thickness | 5 microns | 10 microns | 20 microns |
| 0 | S/V = 2.4 | S/V = 1.2 | S/V = 0.6 |
| 10% | S/V = 4.7 | S/V = 2.3 | S/V = 1.2 |
| 30% | S/V = 38 | S/V = 19 | S/V = 9.4 |

The surface area to volume ratio numbers in Table 6 must be taken in the context of the capsule thickness. Microspheres with a capsule thickness of zero are composed entirely of active drug; there is by definition no inactive ingredient forming a capsule layer. Therefore, even though a 10 μm microsphere with zero capsule thickness has the same surface area to volume ratio (1.2) as a 20 μm microsphere with a 10% capsule thickness, release of active drug from the 20 μm sphere will occur only after the outer layer has dissolved whereas active drug from the 10 μm sphere in this example will begin to be released as soon as microsphere dissolution begins.

In addition, in the context of this invention, high surface area to volume values do not necessarily mean faster release of active drug into the area surrounding the implant. This is because, for the case of non-zero capsule thickness microspheres, the outer material is an inactive ingredient.

By having a formulation in which a distinct capsule thickness is present in microspheres of a distinct size, a true programmable controlled release profile can be engineered by selecting (a) the capsule thickness and microsphere size and (b) by selecting in which proportions different populations of microspheres selected in (a) are combined and bound to the implant (e.g. screw) or other device.

For example, a slow release antibiotic formulation bound to indentations on a screw could consist of ⅓ zero capsule thickness 5 μm microspheres for rapid release, ⅓ 10% capsule thickness 10 μm spheres for intermediate release and ⅓ 10% capsule thickness 20 μm microspheres for long term release as part of a single formulation. Because the capsule of inactive material must be largely dissolved before active drug release, this approach has the distinct advantage of minimizing the overlap of delivery by the various formulation components. This allows the aggregate PK profile of the formulation to be formed by superposition of the release profiles of the components of the formulation.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of treating osteomyelitis, comprising:
   implanting an orthopedic implant into a surgical wound site;
   administering to the wound site a formulation comprised of a plurality of particles which particles are comprised of an antimicrobial drug and a biocompatible polymer; and
   allowing drug from the formulation to dissolve into the wound site over a period of time not less than one day and not more than seven days and provide a therapeutically effective dose of the drug over the period of time to thereby treat osteomyelitis.

2. The method of claim 1, wherein the therapeutically effective dose is in a range of 30 micrograms per milliliter±25 micrograms per milliliter and the period of time is 72 hours±12 hours.

3. The method of claim 2, wherein the therapeutically effective dose is at substantially undetectable levels at more than 5 cm from the wound cite.

4. The method of claim 1, further comprising:
   administering thrombin to the wound cite.

5. The method of claim 1, wherein the formulation comprises:
   a first group of spherical particles comprising 100 or more particles wherein each particle of the first group has the same diameter as other particles in the first group with a margin of error of ±10% or less;
   a second group of spherical particles comprising 100 or more particles wherein each particle of the second group has the same diameter as other particles in the second group with a margin of error of ±10% or less;
   wherein particles of the first group dissolve at a rate which is faster than a rate at which the particles of the second group dissolve and the formulation provides from 5 mcg/ml to 100 mcg/ml of antimicrobial drug to a target area.

6. The method of claim 5, wherein the formulation further comprises:
   a third group of spherical particles comprising 100 or more particles wherein each particle of the third group has the same diameter as other particles in the third group with a margin of error of ±10% or less;
wherein particles of the third group dissolve at a rate different from a rate at which the particles of the first and second groups dissolve.

7. The method of claim 1, wherein the biocompatible polymer is polylactic glycolic acid (PLGA), the antimicrobial is an amino glycoside, and the particles are dispersed in a gel.

8. The method of claim 5, wherein the formulation further comprises:
a plurality of additional groups of spherical particles comprising 100 or more particles wherein the particles of each additional group has the same diameter as other particles in that group with a margin of error of ±20% or less;
wherein particles of each additional group dissolve at a rate different from a rate at which the particles of other groups dissolve.

9. The method of claim 6,
wherein the second group of particles have 1,000 square centimeters or more of surface area per 0.1 cm$^3$ of total particle volume per group of particles more than the first group of particles; and
wherein the third group of particles have 2,000 square centimeters or more of surface area per 0.1 cm$^3$ of total particle volume per group of particles more than the second group of particles.

10. The method of claim 6,
wherein the second group of particles have 5,000 square centimeters or more of surface area per 0.1 cm$^3$ of total particle volume per group of particles more than the first group of particles; and
wherein the third group of particles have 10,000 square centimeters or more of surface area per 0.1 cm$^3$ of total particle volume per group of particles more than the second group of particles.

11. The method of claim 8, wherein the particles of each group dissolve at a rate per unit of time which is different from a rate of dissolution of any other of the groups of particles by an amount of about 25% or more.

12. The method of claim 1, wherein the antimicrobial drug is gentamicin and the particles are in an aqueous solution comprising thrombin.

13. The method of claim 8, wherein the spherical particles in each group have a diameter in a range of from about 40 micrometers to about 2 micrometers.

14. The method of claim 8, wherein the spherical particles in each group have a diameter in a range of from about 30 micrometers to about 4 micrometers.

15. The method of claim 6,
wherein the second group of particles have 1,000 square centimeters or more of surface area per 0.1 cm$^3$ of total particle volume per group of particles more than the first group of particles; and
wherein a third group of particles have 2,000 square centimeters or more of surface area per 0.1 cm$^3$ of total particle volume per group of particles more than the second group of particles.

16. The method of claim 6,
wherein the second group of particles have 5,000 square centimeters or more of surface area per 0.1 cm$^3$ of total particle volume per group of particles more than the first group of particles; and
wherein a third group of particles have 10,000 square centimeters or more of surface area per 0.1 cm$^3$ of total particle volume per group of particles more than the second group of particles.

* * * * *

UNITED STATES PATENT AND TRADEMARK OFFICE
CERTIFICATE OF CORRECTION

PATENT NO. : 8,138,157 B2  
APPLICATION NO. : 12/758602  
DATED : March 20, 2012  
INVENTOR(S) : Reid M. Rubsamen Page 1 of 1

It is certified that error appears in the above-identified patent and that said Letters Patent is hereby corrected as shown below:

On the title page item (57), should read:

A formulation comprised of particles which may be in groups and are comprised of a biocompatible polymer and an antimicrobial drug for controlled release of the drug is disclosed. The particles may be in an aqueous solution comprising thrombin and be dispersed in a gel. The formulation is administered to an area such as an open wound having an orthopedic implant therein and provides a therapeutically effective level of drug to the patient over a therapeutically effective period of time.

In claim 3, line 46, please replace the word "cite" with --site--;

In claim 4, line 48, please replace the word "cite" with --site--.

Signed and Sealed this  
Nineteenth Day of June, 2012

David J. Kappos  
*Director of the United States Patent and Trademark Office*

UNITED STATES PATENT AND TRADEMARK OFFICE
CERTIFICATE OF CORRECTION

| | | |
|---|---|---|
| PATENT NO. | : 8,138,157 B2 | Page 1 of 1 |
| APPLICATION NO. | : 12/758602 | |
| DATED | : March 20, 2012 | |
| INVENTOR(S) | : Reid M. Rubsamen | |

It is certified that error appears in the above-identified patent and that said Letters Patent is hereby corrected as shown below:

On the title page item (57), should read:

A formulation comprised of particles which may be in groups and are comprised of a biocompatible polymer and an antimicrobial drug for controlled release of the drug is disclosed. The particles may be in an aqueous solution comprising thrombin and be dispersed in a gel. The formulation is administered to an area such as an open wound having an orthopedic implant therein and provides a therapeutically effective level of drug to the patient over a therapeutically effective period of time.

Column 28, line 46 (Claim 3, line 3) please replace the word "cite" with --site--;

Column 28, line 48 (Claim 4, line 2) please replace the word "cite" with --site--.

This certificate supersedes the Certificate of Correction issued June 19, 2012.

Signed and Sealed this
Seventeenth Day of July, 2012

David J. Kappos
*Director of the United States Patent and Trademark Office*